(12) United States Patent
Knox et al.

(10) Patent No.: US 9,248,149 B2
(45) Date of Patent: *Feb. 2, 2016

(54) METHODS FOR TREATING A NEOPLASTIC DISEASE IN A SUBJECT USING INORGANIC SELENIUM-CONTAINING COMPOUNDS

(71) Applicant: THE BOARD OF TRUSTEES OF THE LELAND STANFORD JUNIOR UNIVERSITY, Palo Alto, CA (US)

(72) Inventors: Susan J. Knox, Stanford, CA (US); Bryan Husbeck, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/553,866

(22) Filed: Nov. 25, 2014

(65) Prior Publication Data

US 2015/0147413 A1    May 28, 2015

Related U.S. Application Data

(63) Continuation of application No. 10/576,568, filed as application No. PCT/US2004/037572 on Nov. 12, 2004, now Pat. No. 8,932,649.

(60) Provisional application No. 60/520,539, filed on Nov. 14, 2003.

(51) Int. Cl.
| | |
|---|---|
| *A61K 33/04* | (2006.01) |
| *A61K 45/06* | (2006.01) |
| *A61N 5/10* | (2006.01) |
| *A61P 35/00* | (2006.01) |

(52) U.S. Cl.
CPC ............. *A61K 33/04* (2013.01); *A61K 45/06* (2013.01); *A61N 5/1001* (2013.01); *A61N 2005/1098* (2013.01)

(58) Field of Classification Search
None
See application file for complete search history.

(56) References Cited

U.S. PATENT DOCUMENTS

| | | | |
|---|---|---|---|
| 4,665,897 A | 5/1987 | Lemelson et al. | |
| 5,104,852 A | 4/1992 | Kralick et al. | |
| 5,639,787 A | 6/1997 | Riordan et al. | |
| 5,654,328 A | 8/1997 | Sredni et al. | |
| 5,843,481 A | 12/1998 | Cruz et al. | |
| 6,511,971 B1 | 1/2003 | Gorun et al. | |
| 6,656,509 B1 | 12/2003 | Stiefel et al. | |
| 8,932,649 B2 * | 1/2015 | Knox et al. | 424/702 |
| 2002/0107225 A1 | 8/2002 | Gourdeau et al. | |
| 2003/0018066 A1 | 1/2003 | Fleshner et al. | |
| 2008/0081039 A1 | 4/2008 | Corcoran et al. | |

OTHER PUBLICATIONS

Liu, Recent Developments in Diagnosis and Treatment of Nasopharyngeal Carcinoma, Keio J. Med. (1991), vol. 40, No. 2, pp. 59-62.*

Kiremidjian-Schumacher et al. Selenium and Immunocompetence in Patients with Head and Neck Cancer, Biological Trace Element Research (2000), vol. 73, pp. 97-111.*

Abdullaev et al. The Antitumorigenic Effect of Selenium Compounds. Selen. Biol., Mater. Nauchn. Konf. (1974), pp. 126-128. (with Translation).

Baldew et al., "Selenium-induced Protection against *cis*-Diamminedichloroplatinum(II) Nephrotoxicity in Mice and Rats." *Cancer Res.*, 49(11):3020-3 (1989).

Buntzel, "Erfahrungen mit Natriumselenit inder Behandlung von akuten und späten Nebenwirkungen der Radiochemotherapie von Kopf-Hals-Karzinomen." *Med. Klin.*, 3:49-53, 94 Suppl. (1999).

Caffrey et al., "Treatment of human ovarian tumor xenografts with selenite prevents the melphalan-induced development of drug resistance." *Cancer Chemother. Pharmacol.* 46(1):74-8 (2000).

Caffrey et al., "Selenium compounds prevent the induction of drug resistance by cisplatin in human ovarian tumor xenografts in vivo." *Anticancer Res.* 18(4C): 3017-20 (1998).

Caffrey et al., "Prevention of the Development of Melphalan Resistance In Vitro by Selenite." *Biol. Trace. Elem. Res.* 65(3):187-98 (1998).

Caffrey et al., "Sensitivity of melphalan-resistant tumors to selenite in vivo." *Cancer Lett.* 121(2):177-80 (1997).

Clark et al., "Effects of Selenium Supplementation for Cancer Prevention in Patients with Carcinoma of the Skin." *JAMA*, 276: 1957-1963 (1996).

Combs et al., "Chemopreventive Agents: Selenium." *Pharmacol. Ther.*, 79(3): 179-192 (1998).

Combs et al., "Selenium and Cancer Prevention." *Antioxidants and Disease Prevention*, Ch. 8, 97-113. CRC Press, N.Y. (1997).

Cook et al., "Cellular Glutathione and Thiol Measurements from Surgically Resected Human Lung Tumor and Normal Lung Tissue." *Cancer Res.* 51: 4287-4294 (1991).

Corcoran et al., "Inorganic Selenium Retards Progression of Experimental Hormone Refractory Prostate Cancer." *J. Urol.* 171: 907-910 (2004).

Fico et al., "Differential Effects of Selenium on Normal and Neoplastic Canine Mammary Cells." *Cancer Res.* 46: 3384-3388 (1986).

Fleming et al., "Molecular Mechanisms of Cancer Prevention by Selenium Compounds." *Nut Cancer.* 40(1): 42-49 (2001).

Frenkel at al., "A Prevention Strategy for Circumventing Drug Resistance in Cancer Chemotherapy." *Curr Pharm.* 7(16): 1595-614 (2001).

Gasparian et al., "Selenium Compounds Inhibit IκB Kinase (IKK) and Nuclear Factor-κB (NF-κB) in Prostate Cancer Cells." *Mol Canc Ther* 1: 1079-1087 (2002).

(Continued)

*Primary Examiner* — Abigail Fisher
*Assistant Examiner* — Frank Choi
(74) *Attorney, Agent, or Firm* — Shweta Chandra; Bozicevic, Field & Francis, LLP

(57) ABSTRACT

The invention features methods and selenium-containing compositions for treating a neoplastic disease in a subject. In particular, the invention features methods for enhancing sensitivity of a tumor to cancer therapy by treating the tumor with an inorganic selenium-containing (iSe) compound and with a cancer therapy, particularly a cancer therapy that also affects the cellular redox status of a tumor cell (e.g., radiation).

21 Claims, 13 Drawing Sheets

(56) References Cited

OTHER PUBLICATIONS

Ghose et al., "Enhanced Sensitivity of Human Oral Carcinomas to Induction of Apoptosis by Selenium Compounds: Involvement of Mitogen-activated Protein Kinase and Fas Pathways." *Cancer Res*, 61: 7479-7487 (2001).

Ghosh et al., "Rapid induction of apoptosis in prostate cancer cells by selenium: reversal by metabolites of arachidonate 5-lipoxygenase." *Biochem Biophys. Res. Comm.* 315: 624-635 (2004).

Gleave et al., "Progression to Androgen Independence is Delayed by Adjuvant Treatment with Antisense Bcl-2 Oligodeoxynucleotides after Castration in the LNCaP Prostate Tumor Model." *Clin. Cancer Res.* 5: 2891-8 (1999).

Gleave et al., "Targeting bcl-2 Gene to Delay Androgen-Independent Progression and Enhance Chemosensitivity in Prostate Cancer Using Antisense bcl-2 Oligodeoxynucleotides." *Urology.* 54(6A): 36-46 (1999).

Greeder et al., "Factors Influencing the Inhibitory Effect of Selenium on Mice Inoculated with Ehrlich Ascites Tumor Cells." *Science*. 209: 825-827 (1980).

Hehr et al., [Role of sodium selenite as adjuvant in radiotherapy of rectal carcinoma], Med. Klin. (Munich) (1997), vol. 92 Suppl, No. 3, pp. 48,49.

Husbeck et al., "Inhibition of androgen receptor signaling by selenite and methylseleninic acid in prostate cancer cells: two distinct mechanisms of action." *Mol Cancer Ther* 5(8): 2078-2085 (2006).

Husbeck et al., "Tumor-Selective Killing by Selenite in Patient-Matched Pairs of Normal and Malignant Prostate Cells." *The Prostate* 66: 218-225 (2006).

Husbeck et al., "Redox modulation of human prostate carcinoma cells by selenite increases radiation-induced cell killing." *Free Rad Biol Med.* 38: 50-57 (2005).

IP, et al., "Current concepts of selenium and mammary tumorigenesis." *Cellular and Molecular Biology of Breast Cancer*, 479-494. Plenum Press, N.Y. (1997).

Jiang et al., "Distinct Effects of Methylseleninic Acid versus Selenite on Apoptosis, Cell Cycle, and Protein Kinase Pathways in DU145 Human Prostate Cancer Cells." *Mol. Cancer Ther*. 1: 1059-1066 (2002).

Kasseroller et al., "Treatment of secondary lymphedema of the arm with physical decongestive therapy of sodium selenite: a review." *Am J Ther*. 7(4): 273-9 (2000).

Leung et al., "Effect of L-Buthionine Sulfoximine on the Radiation Response of Human Renal Carcinoma Cell Lines." *Cancer*. 71: 2276-85 (1993).

Mackey et al., "bcl-2/bzx Ratio as a Predictive Marker for Therapeutic Response to Radiotherapy in Patients with Prostate Cancer." *Urology*. 52(6): 1085-1090 (1998).

Medina et al., "Current Ideas on Selenium as a Chemopreventive Agent." *Pathol Immunopathol Res*, 7: 187-199 (1988).

Menter et al., "Selenium Effects on Prostate Cell Growth."*Cancer Epid. Biomarkers. Prev.*, 9:1171-1182 (2000).

Micke et al., "Selenium in the Treatment of Radiation-Associated Secondary Lymphedema." *Int. J. Radiation Oncology Biol. Phys.* 56(1):44-49 (2003).

Milner et al., "Inhibitory Effects of Selenium on the Growth of L1210 Leukemic Cells." *Cancer Res*. 41: 1652-1656 (1981).

Milner et al., "Effect of selenium on virally induced and transplantable tumor models." *Fed Proc*. 44: 2568-2572 (1985).

Ohkawa et al., "The effects of co-administration of selenium and *cis*-platin (CDDP) on CDDP-induced toxicity and antitumour activity." *Br. J. Cancer*, 58(1):38-41 (1988).

Pubmed online, file Medline, PMID 9417501 (Hehr et al., [Role of sodium selenite as adjuvant in radiotherapy of rectal carcinoma], Med. Klin. (Munich) (1997), vol. 92 Suppl, No. 3, pp. 48,49), Abstract.

Pubmed online, file Medline, PMID 10554527 (Rodemann et al., [Relevance of the radioprotective effect of sodium selenite], Med. Klin. (Munich) (1999), vol. 94 Suppl, No. 3, pp. 39-41 ), Abstract.

Perry et al., "Glutathione Levels and Variability in Breast Tumors and Normal Tissue." *Cancer*. 72(3): 783-787 (1993).

Rodemann et al., [Relevance of the radioprotective effect of sodium selenite], Med. Klin. (Munich) (1999), vol. 94 Suppl, No. 3, pp. 39-41.

Shamberger et al., "Selenium Distribution and Human Cancer Mortality." *CRC Crit Rev Clin Sci*. 2: 211-219 (1971).

Shen et al., "Superoxide Radical-Initiated Apoptotic Signalling Pathway in Selenite-Treated HEPG$_2$ Cells: Mitochondria Serve as the Main Target." *Free Radic. Biol. Med*. 30(1): 9-21 (2001).

Shen et al., "Dual Role of Glutathione in Selenite-Induced Oxidative Stress and Apoptosis in Human Hepatoma Cells." *Free Radic. Biol. Med*. 28(7):1115-1124 (2000).

Shen et al., "Sodium Selenite-Induced Oxidative Stress and Apoptosis in Human Hematoma HepG$_2$ Cells." *Int. J. Cancer*. 81: 820-828 (1999).

Spallholz. "Selenium and the Prevention of Cancer." *Bulletin of Sellenium—Tellurium Dev. Ass'n* May 2001.

STN online, file CAPLUS, Ace. No. 1976:69542, Doc. No. 84:69542 (Abdullaev et al., Antineoplastic action of selenium compounds, Selen bioi., Mater. Nauchn. Konf. (1974), 126-8, 182-192), Abstract.

Thompson et al., "Comparison of the effects of an organic and an inorganic form of selenium on a mammary carcinoma cell line." *Carcinogenesis* 15(2): 183-186 (1994).

Wachowicz et al., "Selenium compounds in the environment: their effect on human health" *Cell. Mol. Biol. Lett*. 6:375-381 (2001).

Watrach et al., "Inhibition of Human Breast Cancer Cells by Selenium." *Cancer Lett*. 25: 41-47 (1984).

Watrach et al., "Effect of Selenium on Growth Rate of Canine Mammary Carcinoma Cells in Athymic Nude Mice." *Cancer Lett*. 15: 137-143 (1982).

Webber et al., "Inhibitory Effects of Selenium on the Growth of DU-145 Human Prostate Carcinoma Cells in Vitro." *Biochem. Biophys. Res. Commun.*, 130(2):603-609 (1985).

Yuan et al., "Coordinate Alterations in the Expression of BRCA1, BRCA2, p300 and Rad51 in Response to Genotoxic and Other Stresses in Human Prostate Cancer Cells." *The Prostate* 40: 37-49 (1999).

Zhong et al., "Redox-mediated Effects of Selenium on Apoptosis and Cell Cycle in the LNCaP Human Prostate Cancer Cell Line." *Cancer Res*. 61: 7071-7078 (2001).

Zhou et al., "DNA Damage-mediated Apoptosis Induced by Selenium Compounds." *J. Biol. Chem*. 278(32): 29532-29537 (2003).

\* cited by examiner

A

B

C

METHODS FOR TREATING A NEOPLASTIC DISEASE IN A SUBJECT USING INORGANIC SELENIUM-CONTAINING COMPOUNDS

RELATED APPLICATIONS

This application is a continuation of U.S. application Ser. No. 10/576,568 filed in Jan. 3, 2007, issued as U.S. Pat. No. 8,932,649 on Jan. 13, 2015, which application is a National Phase application of PCT/US2004/037572 filed Nov. 12, 2004, which application claims priority to provisional application No. 60/520,539, filed on Nov. 14, 2003.

FIELD OF THE INVENTION

The present invention is in the field of cancer therapy.

BACKGROUND OF THE INVENTION

Although cancer therapies have advanced greatly over the years, significant challenges remain. Cancer therapies are generally associated with undesirable side effects, highlighting the need for therapies that are selective for tumor cells, and thus have decreased toxicity. In addition, chemotherapy- and radiation resistant cancers have a very high hurdle to successful therapy. In some instances, this resistance is due to the resistance of the cancerous cell to apoptosis.

For example, in prostate cancer, the resistance of prostate cancer cells to apoptosis plays a role in local and distant disease progression following conventional therapy (e.g. hormonal ablation and radiotherapy). The durable and local control rate (determined by serum levels of prostate specific antigen (PSA)) for patients with prostatic cancers of various stages and grades treated with primary radiation therapy alone is approximately 38%, and treatment of metastatic disease is palliative at best. The apoptotic machinery of most prostate cancer cells is intact, however, due to molecular alterations the cells are unable to execute the apoptotic pathways.

Selenium, a key component of a number of functional selenoproteins required for normal health, when in the inorganic selenite or an organic form such as selenomethione, has been shown to have both preventive and therapeutic effects. Inorganic and organic selenite can inhibit tumorigenesis in a variety of animal models at doses in excess of those required to support maximal activity of selenoproteins (Ip, et al., Current concepts of selenium and mammary tumorigenesis, In: *Cellular and Molecular Biology of Breast Cancer*, 479-494. Plenum Press, N.Y. (1997); Medina et al., *Pathol Immunopathol Res*, 7: 187-199 (1988); Milner et al., *Fed Proc*, 44: 2568-2572 (1985)). Epidemiology studies have shown a statistically significant inverse relationship between selenium levels and cancer risk (Combs et al., Selenium and cancer, In: *Antioxidants and Disease Prevention*, Ch. 8, 97-113. CRC Press, N.Y. (1997); Shamberger et al., *CRC Crit Rev Clin Sci*, 2: 211-219 (1971)). Human cancer prevention trials have shown that daily oral supplementation with of selenium-enriched yeast containing mostly L-selenomethionine (200 μg/day, approximately four times the recommended daily value) can significantly reduce the incidence of several major cancers including prostate, colon, and lung by nearly 50% (Clark et al., *JAMA*, 276: 1957-1963 (1996)).

While the majority of selenium research has focused on the use of long-term selenium intake for chemoprevention, little attention has been given to the cytotoxic effects of selenium and the potential use of selenium for chemotherapy in the clinical setting. The anti-tumor activities of selenium compounds are dependent upon the dose and chemical form. Selenite (oxidation state +4) undergoes thiol-dependent reduction to selenide ($H_2Se$), which supplies selenium for the synthesis of selenoproteins, whereas selenomethionine is converted to selenocysteine before being degraded by the enzyme β-lyase to $H_2Se$ (Combs et al., *Pharmacol. Ther.*, 79(3): 179-192 (1998)). Selenite metabolism results in the generation of superoxide and oxidative stress through its reductive reaction with reduced GSH (FIG. 1) (Combs, 1998). Selenate is metabolized to selenite in the body.

Selenite is capable of inhibiting cell growth and inducing apoptosis in a variety of human cancer cells lines in vitro (Menter et al., *Cancer Epid Bio Prev*, 9: 1171-1182 (2000); Zhong et al., *Cancer Res*, 61: 7071-7078 (2001)). Selenite (2 mg/kg, subcutaneous injection) has also been shown to inhibit the tumor growth of breast and ovarian cancer cell lines in vivo without apparent ill effects on the host (Watrach et al., *Cancer Letters*, 25: 41-47 (1984); Watrach et al., *Cancer Letters*, 15: 137-143 (1982); Caffrey et al., *Cancer Letters*, 121: 177-180 (1997)). The induction of apoptosis by Selenite is mediated by a redox mechanism involving induction of oxidative stress via superoxide formation and lowered intracellular GSH levels (Zhong, 2001). Mitochondria appear to serve as the main target for Selenite-induced apoptosis, with subsequent release of cytochrome c, followed by mitochondrial depolarization, caspase-3 activation and DNA fragmentation (Shen et al., *Free Rad Biol Med*, 30(1): 9-21 (2001). Several studies have also reported that selenium compounds selectively induce growth inhibition and apoptosis in cancer cells compared to normal cells (Menter, 2000; Fleming et al., *Nut Cancer*, 40(1): 42-49 (2001); Ghose et al., *Cancer Res*, 61: 7479-7487 (2001)). However, the molecular pathways underlying the differential response are poorly understood.

Thus, there remains a need in the field for methods of treating neoplastic disease, particularly drug- and radiation-resistant neoplasms, and particularly for improving the sensitivity of tumors to cancer therapy. The present invention addresses these needs.

LITERATURE

Micke et al., *Int. J. Radiation Oncology Biol. Phys.*, 56(1): 44-49 (2003); Frankel at al., *Curr Pharm* 7(16):1595-614 (2001); Caffrey et al., *Cancer Chemother. Pharmacol.* 46(1): 74-8 (2000); Menter et al., *Cancer Epid. Biomarkers. Prev.*, 9:1171-1182 (2000); Buntzel, *Med. Klin.*, 3:49-53, 94 Suppl. (1999); Caffrey et al., *Biol. Trace. Elem. Res.* 65(3):187-98 (1998); Caffrey et al., *Cancer Lett.* 121(2):177-80 (1997); Baldew et al., *Cancer Res.*, 49(11):3020-3 (1989); Ohkawa et al., *Br. J. Cancer*, 58(1):38-41 (1988); Webber et al., *Biochem. Biophys. Res. Commun.*, 130(2):603-609 (1985); Shen et al., *Int. J. Cancer.* 81: 820-828 (1999); Leung et al. *Cancer.* 71: 2276-85 (1993); Perry et al. *Cancer.* 72(3): 783-787 (1993); Cook et al. *Cancer Res.* 51: 4287-4294 (1991); Mackey et al. *Urology.* 52(6): 1085-1090 (1998); Gleave et al. Clin. Cancer Res. 5: 2891-8 (1999); Gleave et al. Urology. 54(6A): 36-46 (1999); Shen et al. Free Radic. Biol. Med. 30(1): 9-21 (2001); Menter et al. Cancer Epidemiol. Biomarkers Prev. 9: 1171-1182 (2000); Zhong et al. Cancer Res. 61: 7071-7078 (2001); Jiang et al. Mol. Cancer Ther. 1: 1059-1066 (2002); Ghosh et al. Biochem Biophys. Res. Comm 315: 624-635 (2004); Watrach et al. Cancer Lett. 25: 41-47 (1984); Zhou et al. J. Biol. Chem. 278(32): 29532-29537 (2003); Shen et al. Free Radic. Biol. Med. 28(7):1115-1124, 2000; Greeder et al. Science. 209: 825-827 (1980); Watrach et al. Cancer Lett. 15: 137-143 (1982); Milner et al. Cancer Res. 41: 1652-1656

(1981); Caffrey et al. Cancer Lett. 121: 177-180 (1997); Corcoran et al. J. Urol. 171: 907-910 (2004).

SUMMARY OF THE INVENTION

The invention features methods and inorganic selenium-containing compositions for treating a neoplastic disease in a subject. In particular, the invention features methods for enhancing sensitivity of a tumor to cancer therapy by treating the tumor with an inorganic selenium-containing (iSe) compound and with a cancer therapy, particularly a cancer therapy that also affects the cellular redox status of a tumor cell (e.g., radiation).

DEFINITIONS

Figure 1:
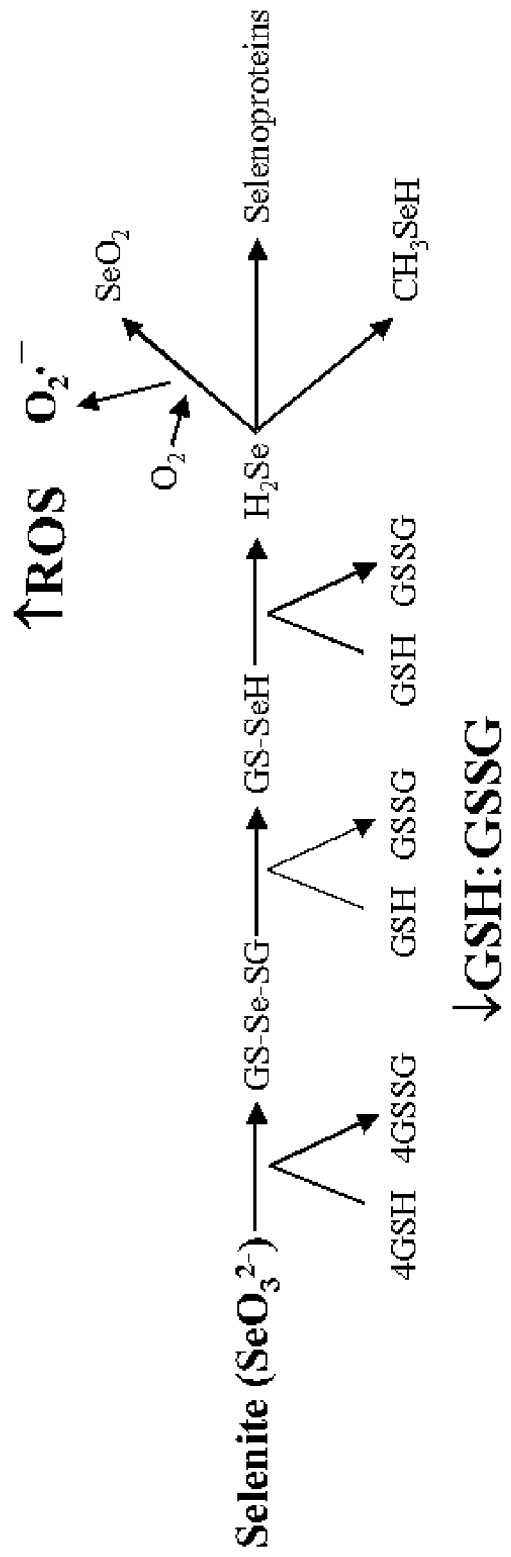
FIG. 1 is a schematic showing how selenite metabolism results in the generation of superoxide and oxidative stress through its reductive reaction with reduced GSH.

By "redox status (or state) of a cell" or "cellular redox status (or state)" is meant the net effect of all oxidizing and reducing agents in the cell, which is largely determined by the level of activity (e.g., expression) of anti-oxidant enzymes in the cell. The redox status of a cell is an important determinant of cellular responses to oxidative damage, including reactive oxygen species (ROS). Most ROS, which can result in oxidative damage originate from endogenous sources as byproducts of normal and essential reactions, such as energy generation from the mitochondria.

"Reactive oxygen species" (ROS) are chemically reactive molecules derived from oxygen and include superoxide ($O_2.^-$), hydrogen peroxide ($H_2O_2$), and the hydroxyl radical (.OH). These highly reactive intermediates can cause damage in numerous biological molecules including proteins, lipids, and DNA. Excessive quantities of ROS can overwhelm the buffering capacity of a cell, and create a pro-oxidant state that predisposes the cell to undergo apoptosis. The alteration of the cellular redox state can also affect the activity of redox-sensitive proteins via the oxidation of critical cysteine residues, which may in turn have downstream effects on signal transduction and gene transcription. The alteration of thiol status may be a key event during apoptosis, and the distribution of thiols in intracellular compartments and in the mitochondrial membrane may modulate the cellular response to oxidative stress.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and can include: (a) preventing the disease or a symptom of a disease from occurring in a subject which may be predisposed to the disease but has not yet been diagnosed as having it (e.g., including diseases that may be associated with or caused by a primary disease); (b) inhibiting the disease or condition, i.e., arresting its development (e.g., as in inhibiting tumor cell viability (e.g., cell division, growth, and the like); and (c) relieving the disease, i.e., causing regression of the disease (e.g., as in facilitating reduction in tumor size, tumor load, and the like), which can result in alleviation of symptoms, reduction of the severity of the disease (up to and including eradication of the disease), cure of the disease, and the like.

The term "synergy" as used herein refers to a response to two or more stimuli that is greater than the sum of the response of the same stimuli applied alone. For example, administration of an iSe compound and, for example, a ROS-inducing cancer therapy (such as radiation) to tumor cells results in greater tumor cell killing (or growth inhibition) than can be explained by the sum of the activity of either agent alone in tumor cell killing (or tumor growth inhibition). Similarly, a "synergistic effect" is an effect that results from such a synergy.

The terms "individual," "host," "subject," and "patient" are used interchangeably herein, and refer to a mammal, including, but not limited to, primates, including simians and humans.

The term "pharmacokinetic profile," as used herein, refers to the profile of the curve that results from plotting serum concentration of a drug over time, following administration of the drug to a subject.

Where a comparative term is used, such as "enhanced", "increased", "decreased", and the like, such terms are used in reference to a suitable control condition. For example, where an iSe compound is said to provide for "enhanced" sensitivity of a cancerous cell to another cancer therapy, such "enhancement" is meant to refer to the sensitivity of the cancerous cells to the cancer therapy in the absence of iSe compound administration. In another example, where it is noted that a cancerous cell has "elevated" GSH levels (e.g., as determined by GSH:GSSG ratio), such "elevation" is meant to refer to a GSH level in a non-cancerous cell, preferably of the same tissue type or origin. The ordinarily skilled artisan will readily appreciate the appropriate comparison to be made when such references are made throughout the present specification.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a compound" includes a plurality of such compounds and reference to "the tumor" includes reference to one or more tumors and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention is based on the discovery that administration of inorganic selenite provides for enhanced sensitivity of a tumor to cancer therapy, such as radiotherapy. Thus the invention features methods and selenium-containing compositions for treating a neoplastic disease in a subject. In particular, the invention features methods for enhancing sensitivity of a tumor to cancer therapy by treating the tumor with an inorganic selenium-containing (iSe) compound and with a cancer therapy, particularly a cancer therapy that also affects the cellular redox status (e.g., generation of ROS) of a tumor cell (e.g., radiation). Combination therapy with an iSe compound and another cancer therapy provides for a synergistic effect in tumor cell killing, which effect is tumor-specific (e.g., the combination does not act in a synergistic manner in killing non-cancerous cells).

The invention for the first time demonstrates that an inorganic selenium containing compound (referred to herein as "iSe compound"), such as inorganic selenite, renders tumors more sensitive to other cancer therapies, such as radiotherapy, especially when administered prior to administration of the second cancer therapy, e.g., so as to allow for iSe metabolism and alteration of the tumor cell redox state with accompanying generation of ROS. Furthermore, the invention also provides a method that provides for a strong preference for killing cancerous cells. The invention finds particular use where the iSe compound is administered in conjunction with, and particular prior to, administration of a cancer therapy that creates or provides reactive oxygen species (ROS) in a cancerous cell.

In addition, the inventors have found that cancerous cells having elevated levels of an antioxidant, such as glutathione (GSH), and/or elevated levels of Bcl-2 expression, are amenable to treatment using iSe compounds, either alone or in conjunction with administration of a cancer therapy.

The inventors' findings have implications for clinical regimens In short, the present invention can provide for administration of lower doses, fewer doses, or both of cancer therapies, as the synergistic effect in killing tumor cells (but not normal, non-cancerous cells) can be exploited to both effect tumor killing while reducing toxicity and associated side effects of cancer therapy.

More specifically, the inventors have found that inorganic selenite induces apoptosis in cancerous cells in a dose-dependent fashion. iSe-induced apoptosis is associated with decreased intracellular GSH:GSSG ratios (reduced glutathione (GSH) to glutathione disulfide (GSSG)). iSe-induced apoptosis in cancer cells appears to be associated with GSH depletion, but GSH depletion is not sufficient for iSe-induced apoptosis. Superoxide production and altered redox signaling as a result of iSe metabolism apparently contribute to iSe-induced apoptosis.

Furthermore, in contrast to apoptosis-inducing agents such as Brefeldin A, normal (non-cancerous) cells are resistant to iSe-induced apoptosis (relative to cancerous cells), while cancer cells were sensitive to iSe-induced apoptosis. Agents such as Brefeldin A do not discriminate between normal and cancerous cells in induction of apoptosis. Moreover, primary cultures of prostate cancer cells were found to have a significantly higher (>3-fold) intracellular GSH:GSSG ratio than those cells derived from matched normal tissue. Thus, the inventors have found a direct relationship between the level of GSH in the cell and the potency of selenite in exerting cytotoxic effects. The rank order of sensitivity to selenite in cells tested coincided with intracellular GSH status.

The inventors have also shown that selenite inhibits Bcl-2 expression and induces Bax-α (mitochondrial targeted Bax) expression in cancer cells, while normal cells, which are more resistant to the effects of iSe, show increased Bcl-2 protein and no change in Bax-α expression in response to iSe. Without being held to theory, levels of manganese superoxidedismutase (MnSOD) may have a protective effect in normal cells, since the inventors observed that, in the context of prostate cancer, normal prostate cells had a significantly higher level of MnSOD expression than prostate cancer cells. Furthermore, and again without being held to theory, the relatively lower level of MnSOD in cancerous cells compared to non-cancerous cells can contribute to the toxic effects of iSe on prostate cancer cells.

Patients having cancerous cells with elevated Bcl-2:Bax ratios (relative to such ratios in non-cancerous cells) are at increased risk of radiation therapy failure. Since the inventors have found that cancerous cells treated with selenite prior to receiving ionizing radiation (IR) showed significantly higher levels of apoptosis compared to cells treated with selenite or IR alone, patients having tumors with elevated Bcl-2:Bax ratios can be particularly amenable to treatment according to the invention.

Thus, the invention also provides a means to assess a patient's tumor, and select a course of therapy that is most likely to succeed. Assessing GSH levels, MnSOD levels, and Bcl-2 levels in cancerous cells of the patient (relative to normal cells of the patient), allows the clinician to select a therapy that is best suited for the patient. The invention in this aspect allows the clinician to avoid administration of therapies doomed to failure. In addition, the methods of treatment according to the invention can provide for a shortened course of treatment that provides for a successful result.

The iSe combination therapy of the invention provides the unexpected advantage that iSe compounds provide for sensitization of tumor cells to cancer therapy (e.g., radiation therapy, chemotherapy, particularly a ROS-inducing cancer therapy)—but not normal cells to a significant degree. In addition, the anti-tumor, tumor-specific effects of iSe compounds are maintained in the presence of the second cancer therapy. Furthermore, and unexpectedly, the effects of combination therapy with an iSe compound and another cancer therapy are synergistic. These phenomenon can operate together to provide for, for example, lower or fewer doses of iSe required to inhibit tumor cell proliferation, tumor growth, or tumor cell survival; lower or fewer doses of the selected second cancer therapy required to inhibit tumor cell proliferation, tumor growth, or tumor cell survival; and lower or fewer doses of both the iSe compound and the second cancer therapy, where the doses are lower or fewer than doses required in a therapy involving administration of an iSe compound or the second cancer therapy alone.

The invention will now be described in more detail.

Inorganic Selenium-Containing Compounds and Formulations

Inorganic selenium-containing compound suitable for use in the invention can be provided in a variety of forms. It is noted that selenium may be present in elemental form or as inorganic or organic selenium compounds. It is also noted that selenium occurs in a number varying valence forms. For example, selenium compounds occur in which the selenium has a +4 valance or a +6 valence, as the selenite and selenate ions, respectively. Preferably, the selenium-containing compound is an inorganic selenium-containing compound, referred to herein as an "iSe compound". It is to be understood, however, that the particular inorganic forms of selenium compounds set forth herein are not to be considered limitative.

Among the inorganic selenite and selenate forms, of interest for use in the compositions of this invention are the water soluble alkali metal salts thereof, and particularly, the sodium and potassium salts, that is, sodium and potassium selenite and selenate. Of particular interest for use in the compositions of this invention are the water soluble alkali metal salts of selenite, and particularly, the sodium and potassium salts, that is, sodium selenite and potassium selenite.

As noted above, selenium compounds may be present in organic forms, which can be referred to as "organoselenium compounds". Exemplary organoselenium compounds include selenium compounds of cysteine and methionine, as well as an organic selenium compound selected from the group consisting of RSeH, RSeR, RSeR', RSeSeR and RSeSeR', wherein R and R' are the same or different and each is an aliphatic residue containing at least one reactive group selected from the group consisting of aldehyde, amino, alcoholic, carboxylic, phosphate, sulfate, halogen or phenolic reactive groups and combinations thereof. Use of organoselenium compounds is less preferred, and may be explicitly excluded from use in the compositions of the invention. Thus, formulations comprising iSe compounds for use in the invention may lack organoselenium compounds in a therapeutically effective amount (e.g., an amount insufficient to effect significant cancerous cell growth inhibition or killing) or lack a detectable organoselenium compounds, such as selenomethionine or selenocystine, and derivatives thereof The iSe compounds for use in the invention are generally water soluble inorganic selenite or selenate compounds, such as alkali metal salts of selenite or selanate. Of particular interest are water soluble inorganic alkali metal selenites, and particularly, the sodium and potassium salts, that is, sodium selenite and potassium selenite. Use of sodium selenite is of particular interest.

iSe compounds are generally administered to a subject in an amount effective to inhibit cancerous cell growth (including cancerous cell killing), preferably with insignificant or relatively little inhibition of normal cell growth (including normal cell killing). In some embodiments, iSe is administered in an amount effective to enhance sensitivy of the cancerous cells to another cancer therapy administered in conjunction with administration of iSe compound.

In exemplary embodiments, iSe can be administered in an amount of, for example, about 0.25 mg/kg, about 0.5 mg/kg, about 1.0 mg/kg, about 1.5 mg/kg, about 3.0 mg/kg, about 6.0 mg/kg, or more with the proviso that a desirable therapeutic index is achieved while providing for alteration of the redox state in the cancerous cell. In some embodiments, iSe compound is administered in amounts ranging from 0.5 mg/kg to 4.0 mg/kg, usually 1.0 mg/kg to 3.0 mg/kg. In some embodiments, the amount of iSe compound administered is greater than 1.7 mg/kg, or greater than 2.0 mg/kg. Doses of iSe are generally greater than that normally associated with use of iSe as a chemopreventive agent, and can be greater than that used in supportive cancer therapy (in which iSe is administered as a protective agent for normal cells in cancer therapy, but not as an anti-cancer agent itself). For example, iSe compounds can be administered at doses greater than 200 µg per day (e.g., for a 75 kb individual, usually by oral administration). Doses of iSe compounds for the therapies of the invention are generally about 10 to 20 fold greater than doses conventionally administered for chemoprevention.

Doses of iSe in accordance with the invention can be administered in whole or divided doses, and can may be administered daily, thrice weekly, twice weekly, weekly, and the like, with daily or weekly dosing being of particular interest. Where iSe compounds are administered in conjunction with another cancer therapy, the iSe dose can be administered at the time of or prior to administration of the cancer therapy and in a dosing schedule that corresponds to the dosing regimen of the other cancer therapy, e.g., so that iSe compound is administered at the time of or prior to each dose of the other cancer therapy.

It will be appreciated that amounts of iSe administered will vary with a variety of factors including, but not limited to, whether the iSe compound is used as a monotherapy (e.g., alone, and not necessarily with other cancer therapies) or in conjunction with another cancer therapy (e.g., radiation, chemotherapy, and the like), form of iSe administered (e.g., selenite or selenate, salt of iSe, and the like), route of administration, formulation, dosage form, severity or extent of disease, tumor type (e.g., localized, metastatic, tissue or origin, and the like), and other factors that will be readily appreciated by a clinician or other health care practitioner.

The therapeutic compositions in accordance with the present invention may be provided in various physical forms, for a variety of methods and routes of administration. For example, the composition can be formulated for, for example, injectable (parenteral), oral, topical, mucosal, and suppository administration. Also of interest are administration by intravenous, intratumoral, tumor targeted, or peritumoral routes, as well as administration to the vasculature of a tumor bed.

The iSe compound-containing compositions of the invention may comprise inert or active additives. For example, the compositions of the can further comprise a suitable pharmaceutically acceptable excipient, which may be a vehicle, carrier, diluent, and/or adjuvant. The compositions can further comprise pharmaceutically acceptable auxiliary substances, such as pH adjusting and buffering agents, tonicity adjusting agents, stabilizers, wetting agents and like, are readily available to the public. The selection of such suitable additional components will depend upon, for example, the form desired, the route of administration, and the neoplastic disease to be treated. The additional components are generally selected so as to not detrimentally affect any of the active ingredients of the composition.

Exemplary inert carriers or vehicles include: sugars and milk sugars, such as lactose; liquids, such as water, isotonic aqueous solutions, saline solutions and alcohol; and inert powders, creams, salves, ointments, cleansing and antiseptic agents and the like.

Exemplary pharmaceutically active additional components may include other cytotoxic agents, e.g., chemotherapeutic drugs, biological response modifiers, or radiosensitizers. As used herein, the term "biological response modifier" (BRMs) refers to compounds which are, in their naturally-occurring state, produced in small amounts as part of the body's natural response to cancer or other diseases. Exemplary BRMs include monoclonal antibodies that bind to antigen of a malignant cells, and which may have an attached cytotoxic molecule (e.g., toxin, radioactive component, etc.); and cytokines (e.g. interferons, interleukins, colony-stimulating factors CSFs) which can stimulate blood cell production and help restore blood cell counts more rapidly after treatment. BRMs can be isolated, naturally-occurring molecules or recombinantly or otherwise artificially produced. Examples of these drugs include, but not limited to Rituxan, HER-2, CMA-676, IFN-α (e.g., IFN-α2a, IFN-α2b, consensus interferon) Interleukin-2, Interleukin-3, Erythropoetin, Epoetin, G-CSF, GM-CSF, Filgrastim, Sargramostim and Thrombopoietin, as well as modified forms (e.g., PEGylated and hyperglycosylated forms) of such molecules. See, e.g., U.S. Patent Publication No. 20020107225, incorporated by reference herein.

In the subject methods, the iSe compounds may be administered to the host using any convenient means capable of resulting in the desired therapeutic effect. Thus, the agents can be incorporated into a variety of formulations for therapeutic administration. More particularly, the iSe compounds, in combination with appropriate, pharmaceutically acceptable excipients (e.g., carriers or diluents), may be formulated into preparations in solid, semi-solid, liquid or gaseous forms, such as tablets, capsules, powders, granules, ointments, solutions, suppositories, injections, inhalants and aerosols. In general, iSe compounds for use in the invention are formulated for enteral administration (e.g., by oral, oral, buccal, or rectal administration), or parenteral administration (e.g., by subcutaneous, intradermal, intraperitoneal, intravenous, or intramuscular administration, e.g., infusion or injection). Administration may also be accomplished by, for example, transdermal, intratracheal, or inhalation administration.

In pharmaceutical dosage forms, the iSe compounds may be administered in the form of their pharmaceutically acceptable salts, or they may also be used alone or in appropriate association, as well as in combination, with other pharmaceutically active compounds. The following methods and excipients are merely exemplary and are in no way limiting.

The iSe compounds can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

In the case of the injectable form of iSe compounds, the compounds may be dissolved in an aqueous buffer to form a parenteral preparation. Suitable aqueous buffers include, but are not limited to, acetate, succinate, citrate, phosphate buffers varying in strength from 5 mM to 100 mM, and distilled or sterilized water. In some embodiments, the aqueous buffer may include sodium chloride, and sugars e.g., mannitol, dextrose, sucrose, glucose and the like.

For oral preparations, the iSe compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Furthermore, the iSe compounds can be made into suppositories by mixing with a variety of bases such as emulsifying bases or water-soluble bases. The suppository can include vehicles such as cocoa butter, carbowaxes and polyethylene glycols, which melt at body temperature, yet are solidified at room temperature. iSe compounds can also be provided in sustained release or controlled release formulations, e.g., to provide for release of agent over time and in a desired amount (e.g., in an amount effective to provide for a desired therapeutic or otherwise beneficial effect).

Unit dosage forms for oral or rectal administration also include, for example, syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

It is to be understood that the particular carriers or vehicles set out above are illustrative only and other known pharmaceutically acceptable materials can be utilized in the compositions of this invention so long as they do not adversely react or interact with the iSe compounds and other active ingredients to destroy the identity or activity thereof. Moreover, the particular carrier or vehicle chosen for use will depend upon the form of the composition needed for the particular method of administration and the host to receive the composition.

In those cases where the composition contains a larger amount of the iSe compound (e.g., in some embodiments more than about 1.0 mg by weight), the composition may be employed in the form of divided dosages when being administered whether it be in the form of a tablet, a capsule or a liquid solution. Moreover, a particular dosage in this respect can be administered several times a day so long as the total amount of iSe compound does not exceed a generally accepted maximum dosage.

In some instances, the composition of this invention can be made by simply mixing the selenium compound in proper proportion with an appropriate carrier. For example, in preparing tablets, an alkali metal selenite or selenate salt in its dry form may be mechanically mixed with a powdered carrier or vehicle and shaped or pressed into tablets or encapsulated by known art recognized techniques. On the other hand, if desirable, such salts can be dissolved in water and then mixed with a powdered carrier and shaped or pressed into tablets.

As an alternative, liquid compositions can be prepared simply by dissolving the iSe compound in water and using the composition in that form with recognized additives for either external or oral application. The materials as mixed should contain a desired amount of iSe, which in a single or divided dose achieve a desired therapeutic effect.

The term "unit dosage form," as used herein, refers to physically discrete units suitable as unitary dosages for human and animal subjects, each unit containing a predetermined quantity of the agents calculated in an amount sufficient to produce the desired effect in association with a pharmaceutically acceptable diluent, carrier or vehicle. The specifications for the unit dosage forms for use in the present invention depend on the particular compound employed and the effect to be achieved, the pharmacodynamics associated with each compound in the host, and the like.

Administration of iSe Compounds as a Monotherapy or in Conjunction with Other Cancer Therapies In one embodiment, the invention provides a method of treating a neoplastic disease in a subject by administering an iSe compound in conjunction with a second cancer therapy, e.g., a cancer chemotherapeutic drug, cancer radiotherapy, and the like. This embodiment may be referred to herein as "iSe combination therapy". The second cancer therapy is preferably one that alters the redox (reduction-oxidation) state of the cell toward oxidation, e.g., through generation of superoxide or other oxidative stress, e.g., by production of reactive oxygen species (ROS), oxidations of antioxidants in the cell (e.g., thiol-containing antioxidants, such as glutathione), and the like.

Exemplary Cancer Therapies for Use in the Invention

Cancer therapies for use in iSe compound combination therapy as described herein can be selected from any available cancer therapy, and selected according to factors such as the cancer type to be treated. Of particular interest is administration of a cancer therapy that creates or provides reactive oxygen species (ROS) in a cancerous cell, particular those that depletes GSH in a cancerous cell. Such cancer therapies are referred to herein as a "ROS-inducing cancer therapy". Preferably, the iSe is administered prior to administration of the cancer therapy. Treatment regimen in the context of iSe combination therapy are discussed in more detail below.

Cancer therapies that can be used in combination with iSe compound therapy include, but are not limited to, DNA damaging agents such as DNA intercalating agents, DNA alkylating agents, and DNA modifying agents, nucleic acid biosynthesis inhibiting agents, apoptosis inducing agents, and mitosis inhibiting agents. Exemplary cancer therapies include, but are not limited to, cyclophosphamide, estramustine, paclitaxel, vinblastine, and cisplatin.

As noted above, administration of a ROS-inducing cancer therapies in conjunction with administration of iSe compounds is of particular interest. Exemplary ROS-inducing cancer therapies include, but are not necessarily limited to, radiation therapy, chemotherapy, photodynamic therapy (also called PDT, photoradiation therapy, phototherapy, or photochemotherapy), administration of ROS-inducing biological response modifiers, and the like.

Where the cancer therapy to be administered is a ROS-inducing chemotherapy, suitable exemplary chemotherapeutic agents include, but are not limited to, inhibitors of glutathione synthesis, inhibitors of other antioxidant enzymes, and inhibitors of the anti-apoptotic Bcl-2 family members, Akt or other important regulators of apoptosis.

Exemplary commercially available compounds include, but are not necessarily limited to: buthionine sulfoximine; anthracyclines, adriamycin (doxorubicin), adriamycinone (doxorubicinone), daunomycin, daunomycinone, daunorubicin, and daunorubicin derivatives such as 5-iminodaunorubicin, ubiquinone, Acid Blues 25, 80, and 41, Acid Green 25, anthraquinone and its derivatives such as 2-bromoanthraquine, 1,2-dihydroxyanthraquinone, 1,8-diaminoanthraquinone, 2,6-diaminoanthraquinone, 1,5-dichloroanthraquinone, 1,2-diaminoanthraquinone, and 2-chloroanthraquinone, quinizarin, anthrarufin, quilalizarin, aloe-emodin and related compounds such as 5-nitro-aloe-emodin, 5-amino-aloe-emodin, 2-allylaloe-emodin, averufin, kalafungin, alizarin complexone dihydrate, quercetin dihydrate, acid black 48, procytoxid, leucotrofina, azimexon, and methoxycin-narnonitrile.

Where the cancer therapy to be administered in conjunction with iSe compound therapy is radiation, radiation therapy can be accomplished according to conventional methods. Such methods include external radiation therapy, brachytherapy (internal radiation therapy), and targeted radiation.

Administration of Cancer Therapy in Connection with iSe Compound Administration

In accordance with the iSe combination therapy of the invention, the second cancer therapy can be administered in conjunction with the iSe compound in a variety of ways. "In conjunction", is meant to encompass administration of iSe prior to or at the time of (preferably, usually not subsequent to) administration of the second cancer therapy. Preferably iSe is administered prior to or at the time of administration of the second cancer therapy, more preferably, iSe is administered prior to administration of the second cancer therapy.

In a particularly preferred embodiment, the iSe is administered prior to the second cancer therapy, and in an amount sufficient to provide for iSe-induced alteration of the tumor cell redox state toward oxidation. The second cancer therapy is then administered after iSe has induced alteration of the tumor cell redox state, e.g., after a time sufficient for metabolism of iSe. The redox state of the tumor cell can be determined by, for example, a reduction in GSH levels in a tumor cell (e.g., a reduction in GSH:GSSH ratio), a decrease in Bcl-2 expression levels (e.g., as detected by a decrease in Bcl-2:Bax expression levels), and the like. For example, second cancer therapy is optimally administered when the ratio of GSH:GSSG in a cancerous cell is reduced least about 25%, 30%, 40%, 50%, 60%, 75%, 85%, 90% or more, usually at least about 50% (relative to prior to iSe compound administration).

The iSe combination therapy of the invention provides the unexpected advantage that iSe compounds provide for sensitization of tumor cells to cancer therapy (e.g., radiation therapy, chemotherapy) but not normal cells to a significant degree, particularly where iSe compound is administered prior to administration of the second cancer therapy. In addition, the anti-tumor, tumor-specific effects of iSe compounds are maintained in the presence of the second cancer therapy. Furthermore, and unexpectedly, the effects of combination therapy with an iSe compound and another cancer therapy are synergistic. These phenomenon can operate together to provide for, for example, lower or fewer doses of iSe required to inhibit tumor cell proliferation, tumor growth, or tumor cell survival; lower or fewer doses of the selected second cancer therapy required to inhibit tumor cell proliferation, tumor growth, or tumor cell survival; and lower or fewer doses of both the iSe compound and the second cancer therapy, where the doses are lower or fewer than doses required in a therapy involving administration of an iSe compound or the second cancer therapy alone.

Neoplastic Disease Amenable to Therapy

Neoplastic disease contemplated for treatment according to the methods of the invention include any abnormal growth of tissue, which may be benign or cancerous, with treatment of cancerous neoplastic disease being of most interest. Reference to "cancer" or "tumor" herein is not meant to be limiting, but only exemplary of the disease to which the therapy of the invention can be applied. Tumors susceptible to therapy according to the invention are generally any tumor that, for example, once sensitized with an iSe compound according to the invention, can be treated using another cancer therapy, particularly so as to provide a synergistic or enhanced effect of the combination of the iSe and cancer therapy.

As discussed above, as well as in the Examples below, normal (non-cancerous) cells are relatively resistant to iSe-induced apoptosis, while cancer cells were sensitive to iSe-induced apoptosis. Furthermore, the inventors have found a direct relationship between the level of GSH in the cell and the potency of selenite in exerting cytotoxic effects. The rank order of sensitivity to selenite in cells tested coincided with intracellular GSH status.

The inventors have also shown that selenite inhibits Bcl-2 expression and induces Bax-α (mitochondrial targeted Bax) expression in cancer cells, while normal cells, which are more resistant to the effects of iSe, show increased Bcl-2 protein and no change in Bax-α expression in response to iSe. Without being held to theory, levels of manganese superoxidedismutase (MnSOD) may have a protective effect in normal cells, since the inventors observed that, in the context of prostate cancer, normal prostate cells had a significantly higher level of MnSOD expression than prostate cancer cells.

Thus, susceptibility of a tumor to treatment using iSe-based therapy and combination therapy can be assessed by assessing the GSH:GSSG ratio or the Bcl-2:Bax expression level ratio in the candidate tumor cells. Tumor cells having elevated GSH levels relative to a normal GSH level (e.g., compared to a matched normal cell control), or having elevated Bcl-2 expression levels relative to a normal Bcl-2 expression level (e.g., compared to a matched normal cell control), are susceptible to iSe-based therapy according to the invention. Methods for assessing GSH levels and for assessing Bcl-2 expression levels are well known in the art, with exemplary assays described in the Examples section below.

Thus, in another embodiment, the invention features, methods for identification of a patient having a tumor susceptible to the iSe combination therapy of the invention. Such methods involve assessing a level of GSH in a cancerous cell of the patient, and comparing the level of GSH in the cancerous cell with a normal level of GSH (e.g., in a normal cell, e.g., a matched normal cell from the same tissue type and the same patient). If the GSH level is greater in the cancerous cell than a normal GSH level, then the patient is amenable to therapy using an iSe combination therapy of the invention. In a related embodiment, GSH levels are assessed by examining the GSH:GSSG ratio (reduced glutathione to glutathione disulfide). Methods for assaying GSH and GSSG are well known in the art.

In a related embodiment, suitable patients for therapy according to the invention are identified by assessing a level of Bcl-2 expression in a cancerous cell of the patient, and comparing the level of Bcl-2 expression in the cancerous cell with a normal level of Bcl-2 expression (e.g., in a normal cell, e.g., a matched normal cell from the same tissue type and the same patient). If the Bcl-2 level is greater in the cancerous cells than in normal cells, then the patient is amenable to therapy using an iSe combination therapy of the invention. Bcl-2 and Bax expression levels can be assessed and the Bcl-2:Bax ratio calculated. Methods for assaying Bcl-2 and Bax expression levels are well known in the art.

In a further related embodiment, the invention provides for identification of a patient suitable for iSe therapy by assessing antioxidant levels in normal cells and in cancerous cells. As noted above, if levels of an antioxidant, such as MnSOD, are higher in normal cells than cancerous cells, the patient is amenable to iSe therapy, as the antioxidant should serve to protect normal patient cells from the effects of the therapy, while at the same time effecting killing of cancerous cells.

In general, the tumors can be solid tumors or lymphohematopoietic tumors. Tumors can be of any tissue origin, grade or stage. For example, the tumors can be associated with cancer of the breast, colon, endometrium, head and neck, lung, skin (e.g., melanoma, basal cell carcinoma, squamous cell carcinoma, and the like), digestive system, gastrointestinal system (including colon, rectum, etc), oral cavity (including lip, mouth, etc.), musculoskeletal system (including muscle, bone, etc.), endocrine system, eye, genitourinary system (e.g., bladder, prostate, ovary, etc.), neurologic system (e.g., brain, etc.), and the like. Both hormone-responsive and hormone-resistant cancers (e.g., androgen-responsive and androgen-resistant prostate cancer; estrogen-responsive and estrogen-resistant breast cancer) and p53 wild type and mutant cancers are of interest for treatment. Treatment of prostate cancer and ovarian cancer, especially cancer therapy resistant prostate and ovarian cancers, are of particular interest, both in the context of administration of iSe compounds alone and in combination therapy (e.g., in conjunction with administration of a second cancer therapy) according to the invention. Such treatment of prostate cancer is of especial interest.

The methods of the invention can be used to treat primary tumors or metastases. In addition, the tumors may be either malignant or benign, with radiation therapy generally being used to treat malignant tumors. The invention finds particular use in the treatment of tumors that are generally recognized as being resistant to therapy or which have proven in a particular patient to be resistant to cancer therapy, e.g., as evidenced by relapse, recurrence, or non-responsiveness to prior cancer therapy. Where the tumor has proved or is known to be resistant to a chemotherapeutic drug, such tumors are often referred to as "drug-resistant" tumors.

Of particular interest are those cancers that are recognized to be or proved resistant to, or relapsed after, administration of a conventional cancer therapy (e.g., radiotherapy, chemotherapy, etc.) that did not include iSe compound combination treatment, particularly where the prior therapy did not involve treatment with an iSe compound followed by administration of a different cancer therapy, according to the invention. Accordingly, treatment of patients who have failed prior therapy ("treatment failure" patients), which patients either initially responded then relapsed (e.g., did not have sustained remission) or who did not significantly respond (e.g., had tumors that proved resistant to conventional therapy), are of particular interest for treatment according to the methods of the present invention. In one embodiment, the goal of invention is to 1) sensitize tumors to a subsequent cancer therapy by administration of an iSe compound; and/or 2) provide for a synergistic effect on tumor growth inhibition by a combination therapy of an iSe compound administered either prior to or with another cancer therapy, particularly a cancer therapy that provides for alteration of tumor cell redox state toward oxidation (e.g., through depletion of GSH levels (e.g., reduction of GSH:GSSG ratio), reduction of Bcl-2 expression levels (e.g., reduction of Bcl-2:Bax expression level ratio), and the like).

Dosing Regimen for iSe Combination Therapy

In general, an "effective amount" of an iSe compound, and particularly where administered alone (e.g., not necessarily in conjunction with a second cancer therapy) is an amount facilitates growth inhibition, up to and including killing, of tumor cells in a subject. Furthermore, in the context of iSe combination therapy, an "effective amount" of an iSe compound is generally an amount that can significantly increase the sensitivity of a tumor to subsequent or concomitant cancer therapy compared to similarly treated tumors without iSe compound treatment (e.g., compared to an expected sensitivity of the tumor type in the absence of iSe compound administration) (P value<0.05).

Where iSe compounds are to be administered prior to administration of another cancer therapy, iSe compounds can be administered according to the invention as early as 2 hours, 6 hours, 12 hours, 24 hours, 2 days, prior to initiation of the second cancer therapy. The second cancer therapy can be administered either as fractionated or single dose therapy, preferably fractionated therapy. Normally iSe compound is administered within about 12 hours, 24 hours, 48 hours, 36 hours, 72 hours prior to the second cancer therapy, usually about 48 hours prior to the second cancer therapy, and can be administered on the same day when the second cancer therapy is initiated.

Precise dosage regimens will vary according to a variety of factors as discussed above, including in this context the course of the second (e.g., subsequent or concomitant) cancer therapy prescribed, and, the iSe compound formulation to be administered.

Where the cancer therapy to be administered in conjunction with iSe compound therapy is radiation, radiation therapy can be accomplished according to conventional methods. Radiation can be administered in a single dose or more commonly in fractionated doses, with the latter being of particular interest. For example, fractionated radiation therapy is generally administered daily, 5 days per week for approximately 2 weeks, 4 weeks, 5, weeks, 7 weeks, 8 weeks, 9 weeks, or more usually for approximately about 2 to 7.5 weeks, with the specific dosing regimen dependent upon a number of factors including the histological type of tumor and stage of disease.

Where the cancer therapy to be administered in conjunction with iSe compound therapy is a chemotherapeutic drug, administration can be accomplished according to conventional methods. The chemotherapeutic drug can be administered in a single dose or in fractionated doses. For example, chemotherapy is generally administered once about every 2 weeks, 3 weeks, or 4 weeks, for a total 4 courses, 5, courses, 6 courses, 7 courses, or 8 courses, with the specific dosing regimen dependent upon a number of factors including the histological type of tumor and stage of disease.

In one embodiment of the invention, administration of iSe compounds enhances tumor sensitivity to cancer therapy such as radiation therapy or chemotherapy, and thus increases the efficacy of conventional cancer therapies. Administration of iSe compounds also provides for enhancement of cancer therapy in a manner that is more specific to tumor cells, i.e., administration of iSe compounds does not significantly increase sensitivity of non-cancerous cells to cancer therapy, e.g., radiation or chemotherapy.

The invention can thus, in some embodiments, allow for shortened courses of cancer therapy, reduction in doses of required for therapy (e.g., reduction in doses of iSe compounds, radiation, chemotherapeutic drugs) required to achieve a given outcome (e.g., compared to a dose required in the absence of iSe compound administration or in the absence of combination therapy with iSe). For example, administration of an iSe compound in conjunction with radiation therapy or chemotherapy may allow the clinician to administer reduced doses of radiation (e.g., about 75%, 80%, or 90-95% of a conventional dose in the absence of iSe combination therapy), with doses that can be increased or decreased as needed (e.g., relative to the apparent sensitivity of the tumor). Alternatively or in addition, administration of an iSe compound in conjunction with radiation therapy or chemotherapy can allow for reduced doses of iSe compounds (e.g., about 75%, 80%, or 90-95% of a conventional dose in the absence of radiation combination therapy). Alternatively or in addition, administration of an iSe compound in conjunction with radiation therapy can allow for shortening of the course of therapy (e.g., by reducing the total number of treatments required to eradicate a tumor by 1, 2, 3, 4, 5, or more)).

In some embodiments, therapy involves administration of an amount of iSe compound and dose of a cancer therapy effective to eradicate the tumor when treating with curative intent or achieve local control/palliate symptoms when treating with palliative intent. For example, therapy according to the invention can involve killing all of the tumor cells in the radiation field, shrinking the tumor by killing some of the cells, or controlling tumor growth (e.g., so as to maintain the tumor at its size at the initiation of therapy), by decreasing or delaying tumor growth.

The effectiveness of iSe compound in potentiating radiation therapy or chemotherapy, or otherwise providing for a synergistic effect due to the combination therapy, can be assessed by conventional methods. For example, tumor size (e.g., tumor volume) can be assessed by physical examination in some cases and by the use of imaging techniques such as MRI, CT, ultrasound, PET and the like.

iSe compound combination therapy (i.e., iSe compounds administered in conjunction with radiation therapy, chemotherapy, or both) can be combined with other treatment regimens as desired, and may be particularly useful in subjects receiving combined modality therapy (either sequential or concurrent chemo and radiation therapy, with or without biological response modifiers). For example, iSe compounds can be administered in conjunction with both a chemotherapy treatment and with radiation therapy, either as separate or combined therapies. For example, a patient may receive an iSe compound, then radiation therapy; an iSe compound, then chemotherapy; an iSe compound, then chemotherapy, and then radiation therapy; an iSe compound, then radiation therapy, then chemotherapy, or an iSe compound together with both chemotherapy and radiation therapy.

Kits

Kits with unit doses of a subject iSe compound-containing formulations suitable for use in the invention, e.g., in injectable dose(s), are provided. In such kits, in addition to the containers containing the unit doses will be an informational package insert describing the use and attendant benefits of the iSe compound formulations in treating neoplastic disease when administered in conjunction with a second, suitable cancer therapy. The kit can include, for example, dosing regimen for the iSe compound formulation and for a variety of second, suitable cancer therapies, where the dosing regimen is one that provides for the most enhanced or synergistic effect of the combination therapy.

In some embodiments, a subject kit includes a container comprising a solution comprising a unit dose of an iSe compound formulation, particularly sodium selenite, and a pharmaceutically acceptable excipient; and instructions to administer a unit dose according to a desired regiment or exemplary regiment dependent upon tumor type, age, weight, second cancer therapy (e.g., radiotherapy, chemotherapy, etc.) and the like. Providing iSe compound formulation suitable for intravenous administration is of particular interest, and in such embodiments the kit may further include a syringe or other device to accomplish such administration, which syringe or device may be pre-filled with the iSe compound formulation. The instructions can be printed on a label affixed to the container, or can be a package insert that accompanies the container.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Examples 1-4

Effects of Selenite on Prostate Cancer Cells

The following examples present analysis of the effects of selenite on LAPC-4 prostate cancer cells, DU-145 prostate cancer cells, and matched pairs of primary prostate (normal and cancer) cell strains in vitro. Prostate cancer cells were found to be significantly more sensitive to selenite-induced apoptosis than normal prostate epithelial cells. Without being held to theory, the data presented below from mechanistic studies suggest that the differential response of normal and cancer cells is due, at least in part, to differences in the relative expression of antioxidants (GSH and MnSOD) and Bcl-2 and DU-145 family members. Furthermore, the data below show that selenite can sensitize LAPC-4 cells to γ-irradiation. In addition, synergistic effects of selenite and radiation in delay of tumor growth were observed in a non-human animal model.

Material and Methods

The following materials and methods are used in the Examples below.

Cell Cultures and Treatments. LAPC-4 prostate cancer cells (provided by Dr. Charles Sawyers, UCLA) were cultured in phenol red free RPMI 1640 (Life Technologies, Rockville, Md.) supplemented with 10% fetal bovine serum (Gemini Bio-Products, Woodland, Calif.) at 37° C. in a humidified atmosphere with 5% $CO_2$.

Primary prostate epithelial cell strains from normal prostate (PZ) and prostate cancer (CA) tissue were provided by Dr. Donna Peehl (Stanford University) using well established methods she has previously described (Peehl, Human prostatic epithelial cells. In: *Culture of Epithelial Cells*, 2$^{nd}$ edition, Freshney, R. I. and Freshney, M. G. (eds.), Wiley-Liss, Inc., N.Y., 171-194 (2002)). Three matched pairs of normal and cancer cell strains were available for study (E-PZ/CA-1, E-PZ/CA-2, and E-PZ/CA-3). Normal cell strains were obtained from a region of the prostate peripheral zone not involved in cancer. E-CA-1, E-CA-2, and E-CA-3 cell strains were derived from prostate carcinomas. Cells were treated at 50-70% confluence.

DU 145 prostate cancer cells (American Type Culture Collection, Rockville, Md.) were cultured in RPMI 1640 (+phenol red) supplemented with 10% fetal bovine serum. When the cells reached 50% confluence the media was replaced and selenite was added at the noted concentrations.

Sodium selenite (referred to in the Examples below as "selenite" for convenience) and buthionine sulfoximine (BSO) were obtained from Sigma (St. Louis, Mo.) and prepared in $dH_2O$. A $^{137}Cs$ irradiator was used to deliver γ-irradiation. All chemicals and reagents were supplied by Sigma (St. Louis, Mo.) unless otherwise noted.

Cell proliferation assay. Cells were seeded in 96-well plates (10,000 cells/well) and treated with selenite for 48 hours. Cell survival was assayed using the CellTiter 96 $AQ_{ueous}$ One Solution Cell Proliferation Assay (Promega, Madison, Wis.). The MTS tetrazolium solution was added directly to the wells, incubated at 37° C. for 3 hours, and then the absorbance was read at 490 nm with a 96 well plate reader (Vmax Kinetic Microplate Reader, Molecular Devices, Sunnyvale, Calif.).

Detection of Apoptosis. Flow cytometry analysis (FACS) analysis of propidium iodide (PI)-stained cells was used to quantify the percentage of apoptotic cells as the fraction of cells with a hypodiploid amount of DNA (Sub-$G_1$). Cells were fixed and permeabilized with 100% ice-cold ethanol at 4° C. overnight. The cells were resuspended in 500 µl of buffer (phosphate buffered saline (PBS), 5 mM EDTA) and incubated with 200 µg/ml RNase A for 30 min at room temperature and then 50 µg/ml PI for 10 min at room temperature. The cell cycle distribution was analyzed using Facstar flow cytometry (Becton-Dickinson, San Jose, Calif.). Cleavage of Caspase-3 as a marker of caspase-mediated apoptosis was also detected by immunoblot analysis (see below).

Western Blot Analysis. Cells pellets (containing floating and adherent cells) were resuspended in lysis buffer (50 mM HEPES pH 7.5, 0.5% NP-40, 0.5% sodium deoxycholate, 50 mM sodium chloride, 1 mM EDTA and 0.1 mM sodium orthovanadate), incubated on ice for 20 min, and spun at 14,000×g to collect whole cell lysates. Protein content was determined using the Dc protein assay (Bio-Rad, Richmond, Calif.). Total cell lysates (15 µg) was run on NuPAGE 10% Bis-Tris gels (Invitrogen, Carlsbad, Calif.). Proteins were transferred to PVDF membranes and blocked with 5% milk/Tris buffered saline (100 mM Tris-HCl pH 7.5, 150 mM NaCl/0.1% Tween 20). Primary antibodies used included rabbit polyclonal anti-caspase-3 (Santa Cruz Biotechnology, H-277, Santa Cruz, Calif.), goat polyclonal anti-actin (Santa Cruz Biotechnology, C-11), rabbit polyclonal anti-MnSOD (Stressgen, SOD-111, Victoria, BC, Canada), mouse monoclonal anti-bcl-2 (Santa Cruz Biotechnology, 100,),), mouse monoclonal anti-bcl-$x_L$ (H-5), and mouse monoclonal anti-bax (Santa Cruz Biotechnology, B-9). The anti-rabbit, goat, and mouse secondary antibodies were conjugated to horseradish peroxidase and detected with ECL western blotting detection reagents (Amersham Biosciences, Piscataway, N.J.).

Determination of Intracellular GSH and GSSG Content. The determination of intracellular GSH and GSSG content following exposure to selenite was performed using the GSH-reductase recycling assay (Vandeputte et al., *Cell Biol Toxicol*, 10: 415-421 (1994)). This assay measures the reaction of GSH with 5,5'-dithiobis(2-nitrobenzoic acid) (DTNB). Briefly, cells (floating and adherent) were rinsed in cold stock buffer (143 mM sodium phosphate, 6.3 mM EDTA, pH7.4), and lysed by repeated freeze thawing in 130 µl of 10 mM HCl. Following lysis a 10 µl sample was removed and used for protein determination. Proteins were precipitated on ice for 15 min with 30 µl of 6.5% sulfosalicyclic acid and centrifuged for 15 min at 2000×g and 4° C. The supernatants were collected and stored at −80° C. until assayed. The 96-well plate assay was prepared by mixing 20 µl of sample or known GSH standard, 20 µl of stock buffer, 200 µl of reaction buffer (1 mM 5,5'-dithiobis(2-nitrobenzoic acid (DTNB) and 0.34 mM nicotinamide adenine dinucleotide phosphate (NADPH) in stock buffer), and 40 µl of GSH reductase (8.5 U/ml). The reaction was recorded kinetically at 30-sec intervals for 6 min at a wavelength of 405 nm GSSG was measured following GSH derivatization with 2-vinylpyridine and triethanolamine. GSSG was measured as described above using known GSSG standards. The concentration of GSH and GSSG was expressed as nmol/mg of protein.

Clonogenic Survival Assays. In Examples 1-4 below, LAPC-4 cells were treated with or without selenite for 6 hours prior to receiving 2 Gy of ionizing radiation. In other Examples, LAPC-4 and DU 145 cells were treated with 10 µM selenite for 6 or 12 hours treatment with 2 or 5 Gy of γ-irradiation.

Following irradiation cells were trypsinized, counted, and seeded in triplicate into 60 mm dishes. At least two dilutions of cells were used for each treatment group. Plated cells were allowed to grow for 14 or 17 days before being stained with 0.25% crystal violet in 75% ethanol. Resulting colonies with greater than 50 cells were scored. The surviving fraction was calculated as the plating efficiency of treated cells divided by the plating efficiency of untreated cells. $SF_2$ is the survival fraction of exponentially growing cells that were irradiated at the clinically relevant dose of 2 Gy. The $SF_2$ enhancement ratio ($SF_2$ ER) is defined here as the $SF_2$ without treatment divided by the $SF_2$ for cells treated with selenite.

Example 1

Selenite Effects on Apoptosis in LAPC-4 Prostate Cancer Cells and Primary Prostate (Normal and Cancer) Cell Strains and the GSH:GSSG Ratio as a Measure of Apoptotic Potential LAPC-4 cells were chosen for these studies because they share many biologically relevant features with newly diagnosed prostate cancer in patients (e.g. expression of prostate specific antigen (PSA), androgen receptor (AR), prostatic acid phosphatase and wild-type p53) (Sawyers et al., U.S. Pat. No. 6,365,797). Selenite induced apoptosis in a dose-dependent fashion in LAPC-4 prostate cancer cells at 48 hours in vitro. Apoptosis was measured with the DNA binding dye propidium iodide, which measures cells in the sub-G1 fraction of the cell cycle as they undergo apoptosis.

Figure 2:
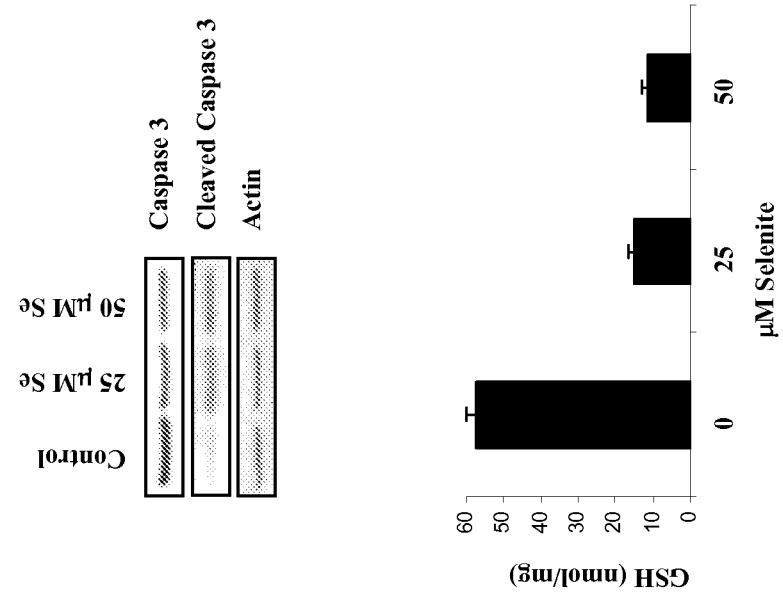
FIG. 2 shows the results of analysis of selenite-induced apoptosis in LAPC-4 prostate cancer cells. Panel A: Cells were treated with selenite at the indicated concentrations for 48 hours (closed squares, selenite alone; open squares, pretreatment with buthionine sulfoximine (BSO) (500 µM) for 24 hours). Percent apoptosis was detected as the fraction of cells in sub-$G_1$ by FACS analysis of PI stained cells. Panel B: Caspase 3 cleavage in LAPC-4 cells following exposure to selenite as detected by Western blot analysis. Panels C and D Ratio of GSH:GSSG (reduced glutathione to glutathione disulfide) and total GSH concentrations in LAPC-4 cells following 48 hour selenite treatment measured using the GSH-reductase recycling assay. Values represent the mean±SD for 3 individual experiments.
Figure 2:
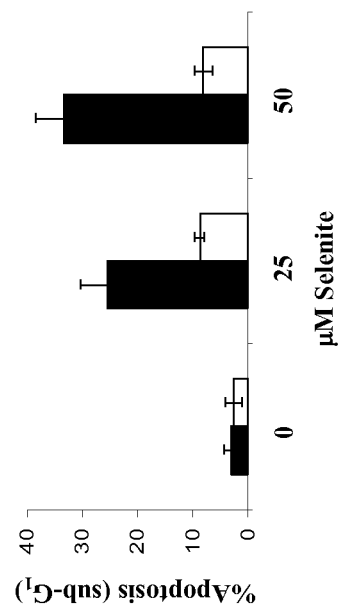
Figure 2:
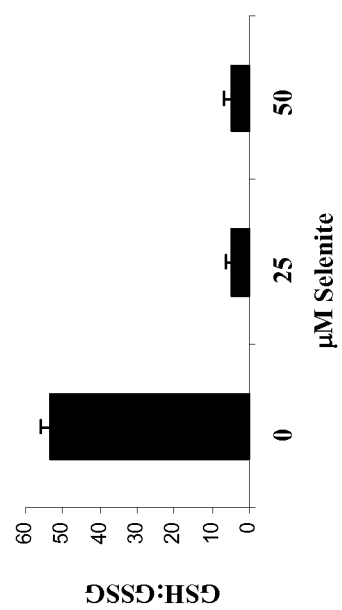

LAPC-4 cells pre-treated with 500 µM BSO for 24 hours, showed decreased selenite-induced apoptosis, suggesting GSH acts as a selenite cofactor that facilitates cell death (FIG. 2, Panel A). Selenite treated LAPC-4 cells also showed a significant increase in cleaved caspase 3 (FIG. 2, Panel B). The induction of apoptosis by selenite in LAPC-4 cells was associated with a decrease in the intracellular ratio of GSH: GSSG as well as the total GSH (FIG. 2, Panels C and D). Interestingly, treatment of these cells with BSO (500 µM for 72 hrs), which produced a similar decrease in the intracellular GSH content, did not induce significant apoptosis. Therefore, other factors in addition to GSH depletion, such as superoxide production and altered redox signaling as a result of selenite metabolism, appear to contribute to selenite-induced apoptosis. Depletion of GSH alone does not explain or predict the effects of selenite, nor does the ability of a compound to deplete GSH-predict that the compound will have the effects of selenite.

Figure 3:
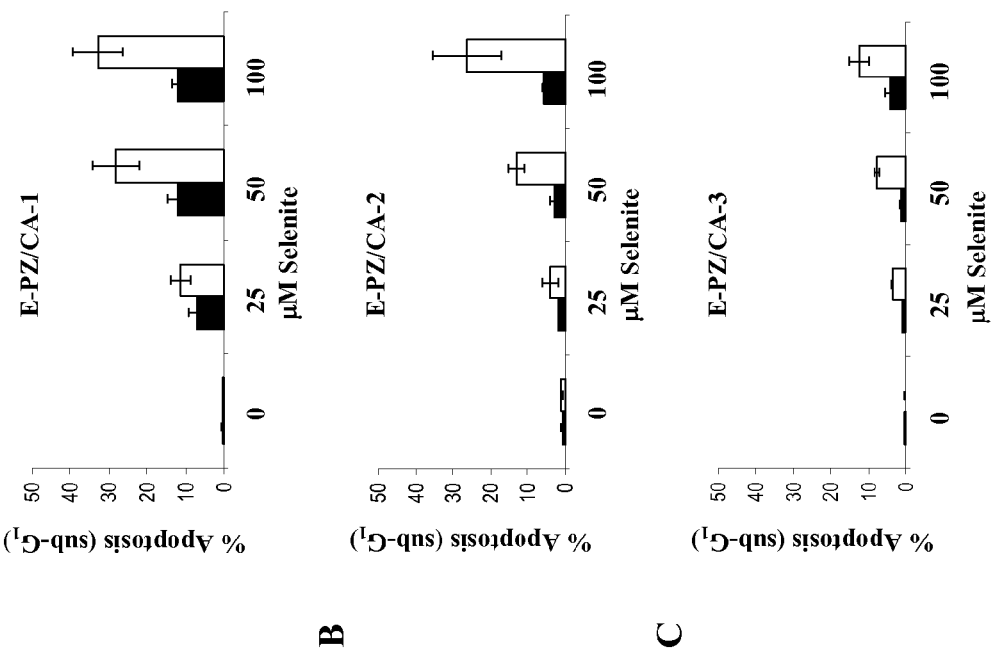
FIG. 3 shows results of analysis of selenite-induced apoptosis in matched pairs of normal prostate and prostate cancer primary cell strains. Cells were treated with selenite for 48 hours and apoptosis was detected as the fraction of cells in sub-$G_1$. Closed squares, normal prostate (PZ); open squares, prostate cancer (CA). Panels A, B, and C: Effects of selenite on matched pairs E-PZ/CA-1, E-PZ/CA-2, and E-PZ/CA-3 respectively. Panel D: Representative examples of cell cycle profiles of E-PZ/CA-3 cells and sub-G1 determinations following selenite treatment. Values represent the mean±SD for 3 individual experiments.

Primary cultures of epithelial cells allow for comparative studies between normal and cancer cells derived from the same subject and cultured under identical conditions (Peehl, 2002). As short-term cultures, primary cultures may also be more realistic models of the behavior of prostate cancer than established cell lines. In experiments in which matched primary cell strains were used, normal prostate cells (from the peripheral zone (PZ), where the majority of prostatic adenocarcinomas originate) were resistant to selenite-induced apoptosis compared to the corresponding prostate cancer derived cells (CA) at 48 hours (FIG. 3, Panels A, B, and C). Normal prostate and prostate cancer cell strains have a similar growth rate in culture (FIG. 3, Panel D), therefore, the differential response to selenite does not appear to be the result of differences in their rate of proliferation.

Figure 4:
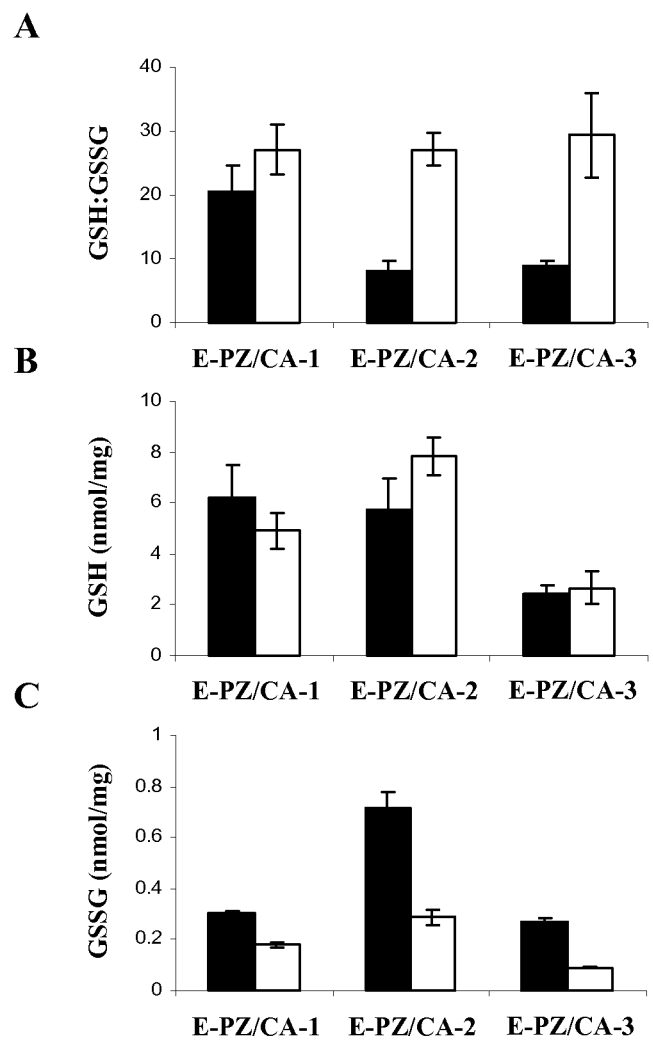
FIG. 4 shows results of analysis of intracellular GSH content in primary prostate (normal and cancer) cell strains. Panel A: The ratios of GSH:GSSG; Panel B: total GSH concentrations, and Panel C GSSG concentrations in E-PZ/CA-1, E-PZ/CA-2, and E-PZ/CA-3 cells measured using the GSH-reductase recycling assay. Closed squares, normal prostate (PZ); open squares, prostate cancer (CA). Values represent the mean±SD for 3 individual experiments.
Figure 5:
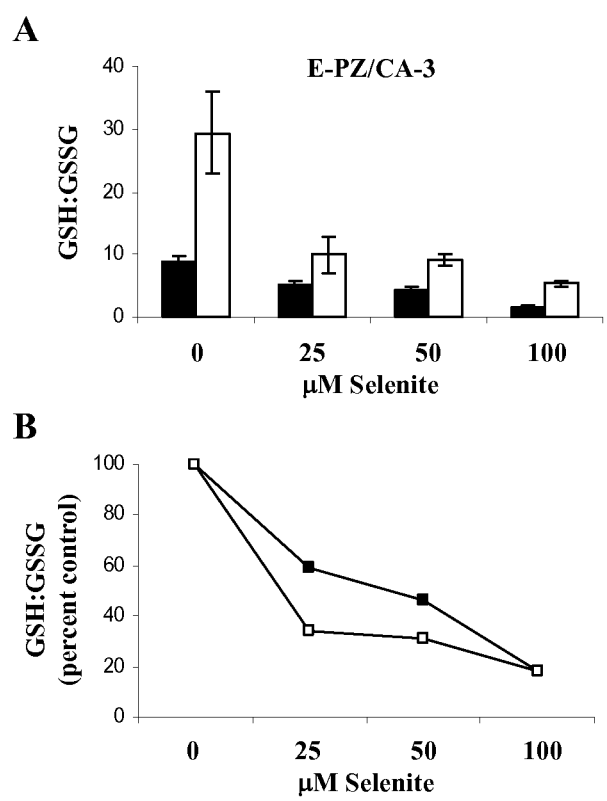
FIG. 5 shows results of analysis of the effects of selenite on the intracellular GSH:GSSG ratio in E-PZ/CA-3 cells. Panel A: Cells were treated with selenite for 48 hours and the ratio of GSH:GSSG was measured using the GSH-reductase recycling assay. Closed squares, normal prostate (PZ); open squares, prostate cancer (CA). Panel B: Percent reduction in the GSH:GSSG ratio following treatment with selenite compared to untreated levels. Values represent the mean±SD for 3 individual experiments.

Prostate cancer cells were found to have higher basal intracellular GSH:GSSG ratios than those cells derived from normal tissue. Total GSH concentrations were similar for each pair of normal and cancer cells, however, there were differences in total GSH between the three different matched pairs (FIG. 4, Panels A, B, and C). The increased ratio of GSH: GSSG in cancer cells was due to the fact that they had significantly less GSSG than the corresponding normal cells. Following treatment with selenite, prostate cancer cells (E-CA-3) showed a greater reduction in the ratio of GSH: GSSG compared to normal cells (E-PZ-3) (FIG. 5, Panels A and B). For example, the GSH:GSSG ratio was decreased 41.1% in normal cancer cells after being exposed to 25 µM selenite for 48 hours, whereas the ratio was decreased 65.9% in the cancer cells. Therefore, selenite appears to have a greater effect upon the intracellular redox state of prostate cancer cells as compared to normal cells. Based upon these results, there appears to be a direct relationship between the level of reduced GSH in prostate cells and the potency of selenite-induced cytotoxicity. The rank order of sensitivity to selenite from lowest to highest, which coincided with intracellular GSH status, was normal human prostate, primary carcinoma, and LAPC-4 prostate cancer cells.

Figure 6:
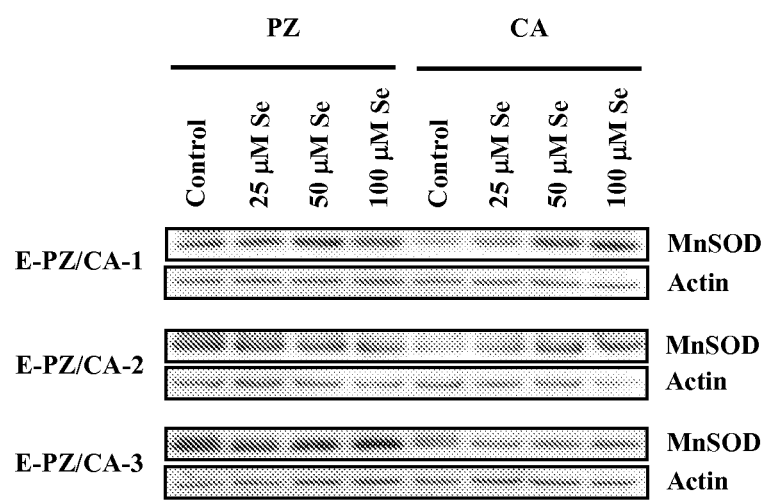
FIG. 6 shows the effects of selenite on intracellular GSH content in LAPC-4 cells. Cells were treated with 10 µM selenite for 6, 24, and 48 hours and total GSH and GSSG concentrations were measured using the GSH-reductase recycling assay. Changes in Panel A, total GSH, Panel B, GSSG, and Panel C, GSH:GSSG are shown after treatment with selenite for 6-48 hours. Values represent the mean±SD for 3 experiments.

In order to assess the intracellular redox state over time, total GSH and GSSG concentrations were measured at 6, 24, and 48 hours after treatment with 10 µM selenite. Selenite decreased total GSH levels in a time-dependent fashion from a basal level of 52.1±5.6 nmol/mg to 11.8±2.1 nmol/mg at 48 hours (FIG. 6, Panel A). The concentration of GSSG increased following selenite treatment and was maximal after 24 hours (FIG. 6, Panel B). As a result, the ratio of GSH: GSSG in LAPC-4 cells was decreased by selenite (FIG. 6, Panel C). As early as 6 hours after treatment with 10 µM selenite, the GSH:GSSG ratio was decreased from 129.4±13.6 to 15.1±2.3. These changes in intracellular GSH content in response to selenite indicate a dramatic shift in the cellular redox balance towards an oxidative state.

Example 2

Selenite-Induced Apoptosis in LAPC-4 Prostate Cancer Cells is Dose-Dependent

Figure 7:
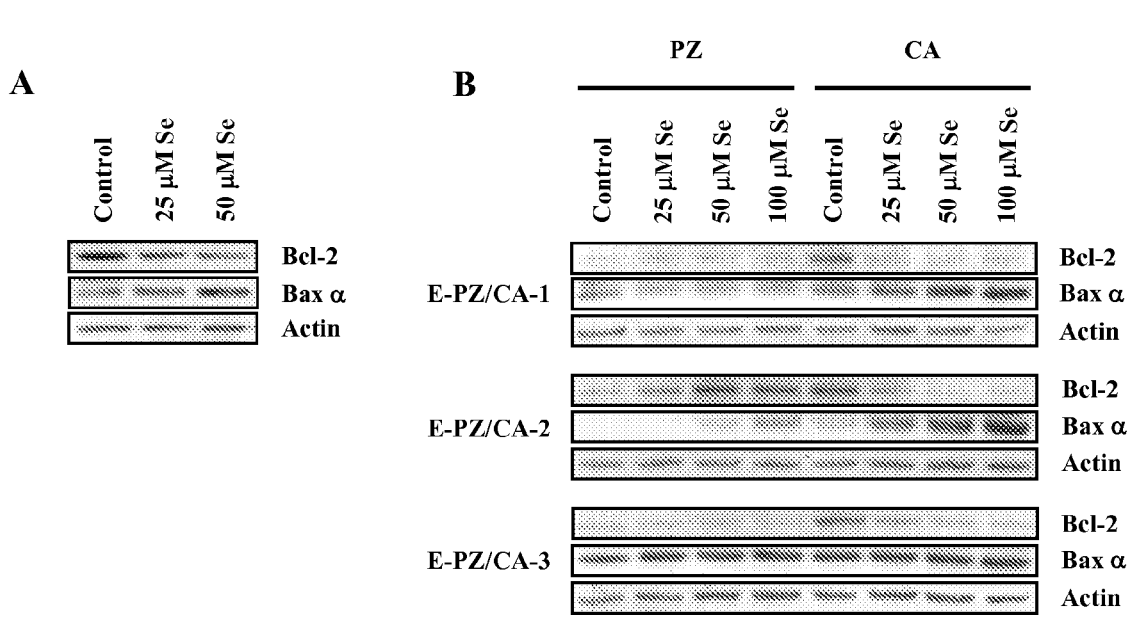
FIG. 7 shows the effects of selenite-induced growth inhibition and apoptosis in LAPC-4 prostate cancer cells and normal prostate cells. Panel A. LAPC-4 cells were treated with selenite at the indicated concentrations for 48 hours and cell proliferation was measured by MTS assay. Panel B. LACP-4 cells were treated with selenite for 48 hours and percent apoptosis was detected as the fraction of cells in sub-$G_1$. Panel C, Caspase-3 cleavage in LAPC-4 cells following exposure to selenite for 48 hours as detected by Western blot analysis. Actin protein expression was used to normalize for loading. Panel D, Primary cultures of normal prostate cells treated with selenite for 48 hours and percent apoptosis was detected. Values represent the mean±SD for 3 experiments.

The proliferation of LAPC-4 cells was measured using the MTS cellular proliferation assay after incubation with selenite for 48 hours. Cell proliferation was 53.3% of control after treatment with 10 µM selenite, and 33.4% of control after treatment with 25 µM selenite (FIG. 7, Panel A). Apoptosis was measured as the percentage of cells in the sub-G1 fraction of the cell cycle. The percentage of sub-G1 cells following treatment with 10 or 25 µM selenite for 48 hours was 14.5% and 26.1%, respectively (FIG. 7, Panel B). Cleavage of caspase-3, a marker of apoptosis, was also detected in selenite-treated LAPC-4 cells by Western blotting (FIG. 7, Panel C). In contrast, primary cultures of normal prostate epithelial cells were more resistant to selenite-induced apoptosis than LAPC-4 cells (FIG. 7, Panel D). These data show that selenite inhibited cell growth and induced apoptosis in a dose-dependent fashion in androgen-dependent LACP-4 human prostate cancer cells in vitro.

Example 3

MnSOD Protein Expression in Primary Prostate Cell Strains

Mangenese superoxide dismutase (MnSOD) is an antioxidant enzyme located in the mitochondrial matrix that scavenges superoxide anions produced as a consequence of aerobic respiration (Pani et al., *Cancer Res*, 60:4654-60 (2000)). Since superoxide is a by-product of selenite metabolism, MnSOD protein expression was measured in normal and cancer cell strains.

Figure 8:
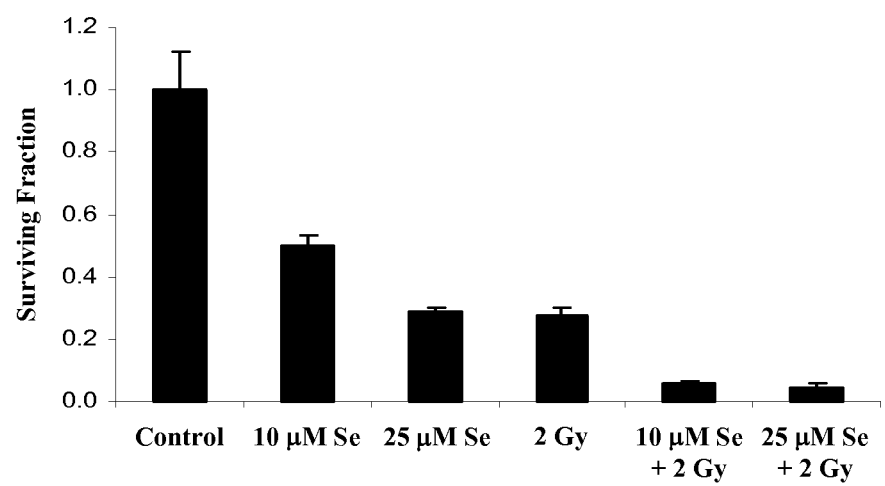
FIG. 8 shows results of analysis of MnSOD protein expression in primary prostate (normal and cancer) cell strains. Western blot analysis of MnSOD protein expression in E-PZ/CA-1, E-PZ/CA-2, and E-PZ/CA-3 cells following 48 hour exposure to selenite. Actin protein expression was used to normalize for loading.

Normal prostate cells had significantly higher basal levels of MnSOD expression than the prostate cancer cells. After selenite treatment for 48 hours the normal cells showed little or no induction of MnSOD protein, whereas in the prostate cancer cells (E-CA-1 and E-CA-2), selenite induced MnSOD protein expression in a dose-dependent fashion (FIG. 8). MnSOD expression is highly inducible by various agents and conditions that cause oxidative stress, which suggests that more ROS is generated in prostate cancer cells in response to Selenite than in normal cells. The difference in basal MnSOD expression may contribute to the differential effects of Selenite in prostate cancer versus normal cells. Relate expression back to original tissues from which they were derived.

Example 4

Effects of Selenite on Bcl-2 and Bax Expression in Normal Prostate and Cancer Primary Cell Strains The Bcl-2 protein family is among many key regulators of apoptosis. Anti-apoptotic Bcl-2 associates with the outer mitochondrial membrane to regulate the mitochondrial membrane potential, counteract the effect of the pro-apoptotic Bax, and block the release of cytochrome c, which is important for apoptotic signaling (Adams et al., Science, 281: 1322-1326 (1998)). Dynamic changes in the Bcl-2:Bax ratio appear to be important in the induction of apoptosis in prostate cancer cells.

Figure 9:
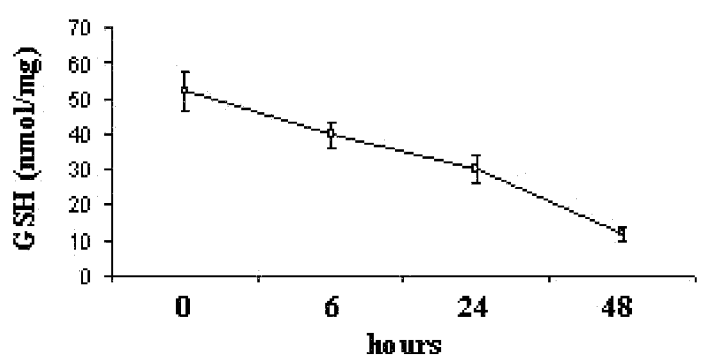
FIG. 9 shows the results of analysis of the effects of selenite on Bcl-2 and Bax protein expression. Western blot analysis of Bcl-2 and Bax a expression in Panel A LAPC-4 and Panel B E-PZ/CA-1, E-PZ/CA-2, and E-PZ/CA-3 cells following treatment with selenite for 48 hours. Actin protein expression was used to normalize for loading.
Figure 9:
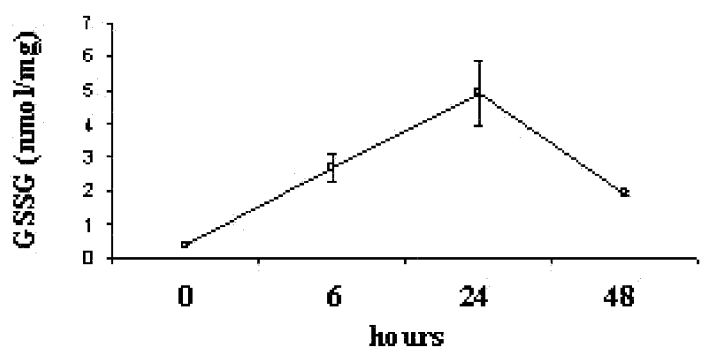
Figure 9:
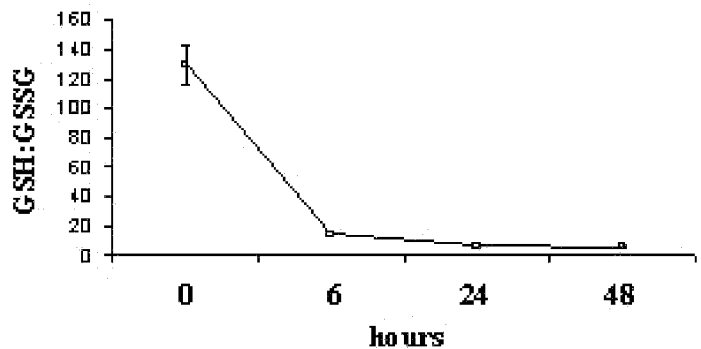

Selenite (48 hours) decreased the Bcl-2:Bax expression ratio in LAPC-4 and primary prostate cancer derived cells (FIG. 9, Panels A and B) Whether the decrease in the Bcl-2:Bax ratio is the result of decreased intracellular GSH and/or increased ROS is not known. In contrast, normal prostate cells, which are more resistant to the effects of selenite, show no change or increased Bcl-2 protein expression and no change or slight induction of Bax-α expression in response to selenite.

Figure 10:
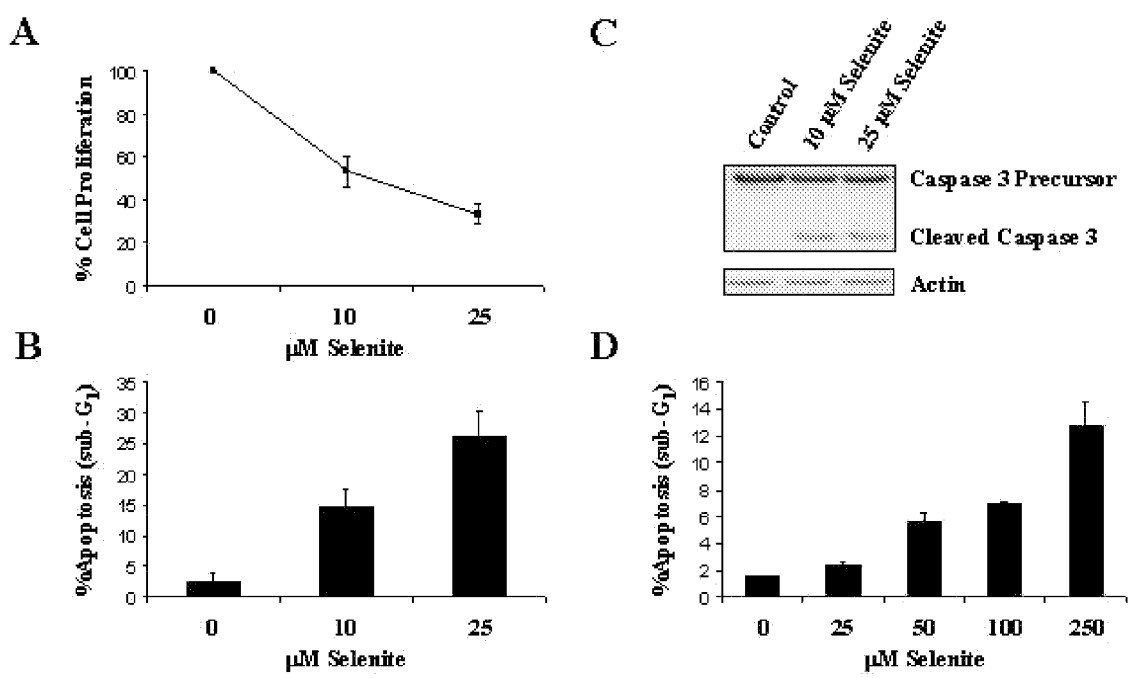
FIG. 10 shows the effects of selenite on bcl-2, bcl-$x_L$, and bax protein expression. Western blot analysis of bcl-2, bcl-$x_L$, and bax-α expression in LAPC-4 cells after treatment with selenite for 48 hours. Actin protein expression was used to normalize for loading.

Expression levels of bcl-2, bcl-$x_L$, and bax were also assessed after exposure to 10 μM and 25 μM selenite selenite for 48 hours by Western blotting (FIG. 10). The expression of anti-apoptotic, bcl-2 and bcl-$x_L$, were decreased following treatment with selenite, and this reduction was coupled to an increased expression of pro-apoptotic bax. The decreased bcl-2:bax expression ratio indicates that selenite-induced apoptosis in LAPC-4 cells correlates with a shift in the balance of Bcl-2 family member expression from a pro-survival to apoptotic state.

Example 5

Selenite Sensitizes LAPC-4 Cells to Radiation-Induced Cell Killing

Figure 11:
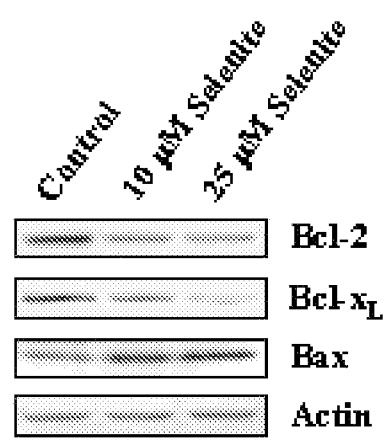
FIG. 11 shows the results of analysis of selenite sensitizes LAPC-4 cells to irradiation. Clonogenic survival data for LAPC-4 cells treated with or without selenite (10 or 25 µM) for 6 hours prior to receiving 2 Gy of irradiation. Colony-forming efficiency was determined 14 days later and surviving fractions were calculated. Values represent the mean±SD for 3 individual experiments.

Prostate cancer patients with elevated Bcl-2:Bax ratios are at increased risk of radiation therapy failure (Mackey et al., *Urology*, 52(6): 1085-1090 (1998)). Since the above examples showed that selenite can decrease the GSH:GSSG and Bcl-2:Bax ratios in LAPC-4 cells, the ability of Selenite to sensitize LAPC-4 cells to γ-irradiation was tested. LAPC-4 cells exposed to 10 μM or 25 μM selenite for 6 hours prior to receiving 2 Gy of ionizing radiation showed significantly decreased survival compared to cells treated with selenite or irradiation alone as measured by clonogenic survival assay (FIG. 11.

Figure 12:
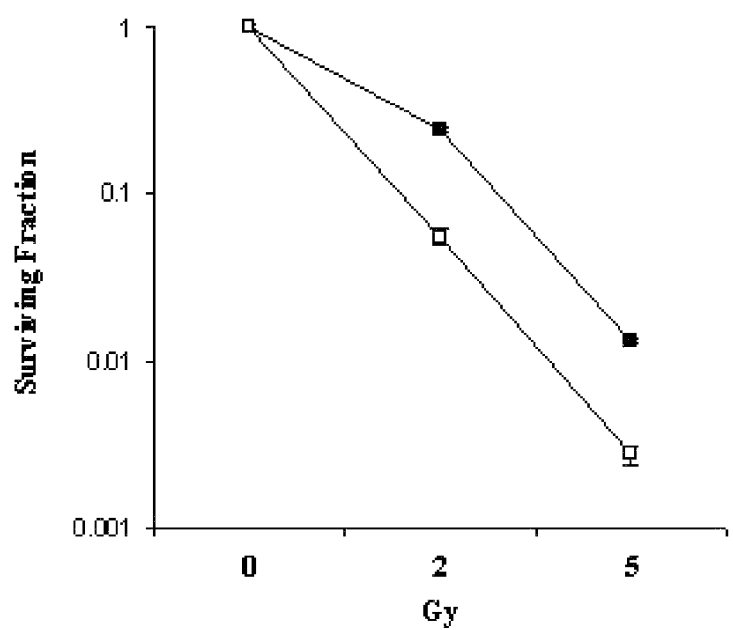
FIG. 12 shows results that illustrate that selenite enhances radiation-induced cell killing in LAPC-4 cells. Clonogenic survival data for LAPC-4 cells treated with radiation alone (closed squares) or 10 µM selenite for 6 hours (open squares) prior to 2 or 5 Gy of γ-irradiation. Surviving fractions were calculated as the plating efficiency of treated cells divided by the plating efficiency of untreated cells. For combination experiments the results were normalized for the killing from selenite alone. Values represent the mean±SD for 3 experiments.

In order to assess the effects of higher doses of γ-radiation, LAPC-4 cells were treated with 10 μM selenite for 6 hours prior to receiving 2 Gy or 5 Gy γ-irradiation. Survival was measured using a clonogenic assay. This treatment regimen was based upon the data above showing that treatment of LAPC-4 cells with 10 μM selenite for 6 hours decreased the GSH:GSSG ratio 88.3%. The surviving fraction of LAPC-4 cells after treatment with selenite alone was 0.431±0.021 (data not shown). In experiments, in which selenite was combined with radiation, the results were normalized for the killing from selenite alone. Selenite enhanced radiation-induced inhibition of colony formation ($SF_2$=0.056) compared to cells treated with radiation alone ($SF_2$=0.244) (FIG. 12). These results indicate that selenite inhibits the clonal growth of LAPC-4 cells and enhances the effect of radiation on these cells.

Example 6

Radiosensitization of Androgen-Independent DU 145 Cells by Selenite

Figure 13:
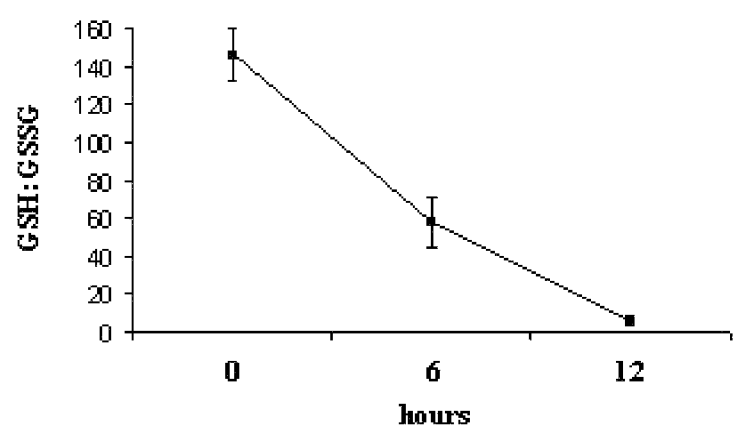
FIG. 13 shows that selenite provides for radiosensitization of DU 145 cells. Panel A, Cells were treated with 10 µM selenite for 6 or 12 hours and changes in the ratio of GSH:GSSG were measured as described previously. Panel B, Clonogenic survival data for DU 145 cells treated with radiation alone (closed squares) or 10 µM selenite for 6 (open squares) or 12 (open triangles) hours prior to γ-irradiation. Surviving fractions were calculated as the plating efficiency of treated cells divided by the plating efficiency of untreated cells. For combination experiments the results were normalized for the killing from selenite alone. Values represent the mean±SD for 3 experiments.
Figure 13:
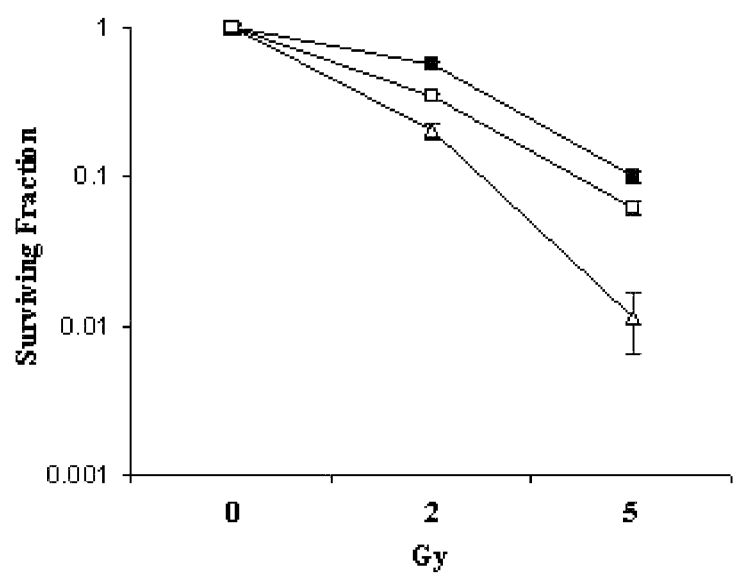

An androgen-independent prostate cancer cell line was examined to determine if selenite would similarly sensitize these cells to γ-irradiation. The androgen-independent DU 145 prostate cancer cell line was chosen because previous studies have shown that selenite can inhibit growth and induce apoptosis in these cells (Shen et al., 1999 *Int. J. Cancer*. 81: 820-828). Again, changes in intracellular GSH and GSSG were measured 6 and 12 hours after treatment with 10 μM selenite. The ratio of GSH:GSSG decreased from a basal level of 146.4±14.0 in controls cells to 57.5±13.8 and 5.7±1.8 at 6 and 12 hours, respectively (FIG. 13, Panel A).

The effects of selenite on the response of DU 145 cells to γ-irradiation were studied using clonogenic survival assays. The surviving fractions of DU 145 cells treated with 10 μM selenite for 6 or 12 hours alone (and assessed at 17 days after irradiation) were 0.941 and 0.409, respectively (data not shown). After normalization for the killing from selenite alone, pre-treatment with selenite enhanced radiation-induced cell death ($SF_2$=0.343 and 0.199 at 6 and 12 hours, respectively) compared to cells treated with radiation alone ($SF_2$=0.554) (FIG. 13, Panel B). These results are summarized in Table 1.

TABLE 1

Radiosensitization of LAPC-4 and DU 145 cells by selenite

| Cell Line | Treatment | $SF_2$ | $SF_2$ ER |
|---|---|---|---|
| LAPC-4 | Radiaton alone | 0.244 | |
| | 10 μM Selenite 6 hr pre Radiation | 0.056 | 4.36 |
| DU 145 | Radiaton alone | 0.554 | |
| | 10 μM Selenite 6 hr pre Radiation | 0.343 | 1.62 |
| | 10 μM Selenite 12 hr pre Radiation | 0.199 | 2.78 |

These data indicate that the iSe and radiation combination therapy of the invention can be useful in enhancing radiosensitivity of hormone-dependent and hormone-independent cancers. Moreover, the combination therapy of the invention can be used to treat cancers having wild-type or mutant tumor suppressor genes. LAPC-4 cells have wild-type p53 and Rb tumor suppressor genes, while DU 145 cells contain mutant p53 and Rb.

Example 7

Analysis of Effect of Inorganic Selenite In Vivo in a Non-Human Animal Model

In vivo studies are performed in scid mice with subcutaneous LAPC-4 xenograft prostate cancer tumors on the upper leg/flank. Mice are injected with $1 \times 10^6$ cells suspended in matrigel. Once the tumors have reached approximately 100-150 $mm^3$ in size, mice are treated with 1, 2 or 4 mg/kg Selenite in phosphate buffered saline by subcutaneous injection three times per week (with 7 mice per group) as described in previous studies (Milner et al., *Fed Proc*, 44: 2568-2572 (1985); Combs et al., Selenium and cancer. In: *Antioxidants and Disease Prevention*, Ch. 8, 97-113. CRC Press, N.Y. (1997); Shamberger et al., *CRC Crit Rev Clin Sci*, 2: 211-219 (1971)).

The length, width, and height (mm) of the tumors are measured with calipers before treatment and three times a week thereafter until the tumor volume is at least (4×) the original pretreatment volume. The animals are sacrificed when the tumors reach the predetermined size. Tumor volume ($mm^3$) are calculated according to the formula: tumor volume=π/6×length×width×height. The data are expressed as percent of the pretreatment volume on day 0, or as the mean tumor volume quadrupling time (TVQT, in days)±standard error, and the tumor growth delay (TGD, in days) time. The TGD time of each group are expressed as the difference between the TVQT of treated tumors compared to that of untreated control tumors. Data are analyzed using a two-tailed Student's t-test. Animal body weight is also recorded as an indicator of toxicity. 2 mice per group are sacrificed at 48 and 168 hours (2 and 7 days) following treatment for measurement of apoptosis and GSH content. In the event of significant tumor shrinkage, tumors are excised at earlier time points. Apoptosis in treated tumors are quantitated by TdT-mediated dUTP nick end labeling (TUNEL) staining of fixed tissue sections using fluorescent microscopy (53). The GSH content within the tumor will also be measured using a GSH-reductase recycling assay.

Example 8

Analysis of Effect of Inorganic Selenite and Radiation Combination Therapy In Vivo in a Non-Human Animal Model A pilot dose finding experiment is performed with 5 mice per group treated with 0, 5, 10, and 15 Gy (local radiation) given as a single fraction to the tumor. Mice are irradiated with a Philips 200 kVp X-ray unit (12.5 mA; half-value layer, 1.0 Cu), at a dose rate of approximately 1.0 Gy/min, in round plexiglass jigs with custom lead block shielding to limit the radiation therapy field to the tumor with margin. A dose that results in measurable tumor shrinkage but not a cure are selected for further study.

For Selenite plus radiation therapy studies, 2 sets of experiments are conducted using A) radiation given as a single dose (as identified above) or B) radiation given in multiple doses (3 Gy per day for 5 days). The first experiments will consist of the following groups: A) untreated control, B) Selenite alone (using a dose regime previously demonstrated to cause the greatest but non-curative reduction in tumor growth from Example 5), C) radiation alone (single dose determined from pilot study) and D) Selenite plus radiation. The second set of experiments include the following groups: A) untreated control, B) Selenite alone, C) radiation alone (fractionated schedule of 3 Gy per day for 5 days) and D) Selenite plus fractionated radiation therapy. Each treatment group contains 10 mice. The same schedule as in Example 6 is used for sacrifice and measurement of specified endpoints. Tumor response data are analyzed as described in Example 6.

Example 9

Evaluation of Therapeutic Index of Selenite Combination Therapy

A net gain in the therapeutic index using selenite as a potential radiosensitizer or chemotherapy sensitizer for the treatment of neoplastic disease requires that selenite not have a similar radiosensitizing effect in normal tissues. The mucosa of the gastrointestinal tract is one of the most radiosensitive tissues in the abdominal/pelvic area. Analysis of effects on mucosa is particularly clinically relevant for the treatment of prostate cancer with radiation, since diarrhea and rectal problems are not uncommon side effects of radiation therapy to the prostate (and regional lymphatics).

The effects of Selenite combined with radiation therapy on gastrointestinal mucosa are assessed using the well characterized and validated intestinal crypt cell survival assay (Franker et al., Methods Cell Biol, 46: 57-76 (1995); Peehl et al., In Vitro, 24: 526-530 (1988)). C3H/SPF mice are used for this analysis, because unlike scid or nude mice, they are immunologically normal and do not have an inherent defect in DNA repair (like scid mice) that would increase the radiosensitivity of normal tissues. The inventors have extensive experience with this assay in this strain of mouse and have previously demonstrated that 12 Gy as a single dose will induce sufficient radiation damage to allow for the detection of either protection or enhanced damage by combining a radiation modulating agent with radiation therapy (Peehl, 1988).

This study has 4 experimental groups: Untreated control, 12 Gy abdominal/pelvis radiation therapy alone, Selenite (at the optimal radiosensitizing dose and schedule identified in the experiments above) and 12 Gy radiation+Selenite. There are 5 mice per group. Male C3H/SPF mice are irradiated with a Philips 200 kVp X-ray unit (as described above) in round plexiglass jigs with custom lead block shielding to limit the radiation therapy field to the abdomen and pelvis. Mice are sacrificed 90 hours after irradiation and the survival of intestinal crypt stem cells are assessed by the microcolonoy method as previously described (Franker, 1995; Peehl, 1988). This method, including the scoring method and statistical method utilized for analyzing this data has been described in detail (Peehl, 1988).

Example 10

Effect of Selenite and Radiation Combination Therapy In Vivo in a Non-Human Animal Model Mice with well-established LAPC-4 tumors were treated with selenite alone, local tumor radiation alone, or selenite with localized tumor radiation. selenite significantly enhanced local radiation-induced tumor growth delay. The effect of the combined treatment was significantly greater than that of radiation or selenite alone. Furthermore, selenite treatment was very well tolerated, and there was no significant weight loss in the selenite treated mice compared to the group of mice treated with local tumor irradiation alone.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating prostate cancer in a subject, the method comprising:
   administering to a subject having prostate cancer a pharmaceutically acceptable salt of an inorganic selenium-containing compound (iSe compound) in an amount effective to alter a reduction-oxidation state of a prostate cancer cell toward oxidation, wherein the administering of the iSe compound is oral; and
   administering radiotherapy to the subject within 6 hours after administering the iSe compound;
   wherein administering the iSe compound and radiotherapy provides for a synergistic effect in treating the prostate cancer in the subject.

2. The method of claim 1, wherein the iSe compound is inorganic selenite.

3. The method of claim 1, wherein the radiotherapy is external beam radiation therapy, brachytherapy or systemically targeted radiation.

4. The method of claim 1, wherein the iSe compound is administered within 2 hours prior to administering the radiotherapy.

5. The method of claim 1, wherein the pharmaceutically acceptable salt of the iSe compound is a sodium salt.

6. The method of claim 1, wherein the iSe compound is inorganic selenate.

7. The method of claim 1, wherein the prostate cancer is androgen-responsive.

8. The method of claim 1, wherein the prostate cancer is androgen-resistant.

9. A method of enhancing sensitivity of prostate cancer in a subject to radiotherapy, the method comprising:
 administering to a subject having prostate cancer a pharmaceutically acceptable salt of an inorganic selenium-containing (iSe) compound in an amount effective to sensitize the prostate cancer to radiotherapy, wherein the administering of the iSe compound is oral; and
 administering the radiotherapy to the subject within 6 hours after administering the iSe compound;
 wherein administration of the iSe compound is effective to enhance sensitivity of the prostate cancer to the radiotherapy.

10. The method of claim 9, wherein inorganic selenium-containing compound is inorganic selenite.

11. The method of claim 9, wherein the radiotherapy comprises external radiation therapy, brachytherapy (internal radiation therapy), or systemically targeted radiation.

12. The method of claim 9, wherein the iSe compound is administered within 2 hours prior to administering the radiotherapy.

13. The method of claim 9, wherein the pharmaceutically acceptable salt of the iSe compound is a sodium salt.

14. The method of claim 9, wherein the iSe compound is inorganic selenate.

15. The method of claim 9, wherein the prostate cancer is androgen-responsive.

16. The method of claim 9, wherein the prostate cancer is androgen-resistant.

17. A method of treating prostate cancer, the method comprising:
 administering to a subject having prostate cancer a pharmaceutically acceptable salt of an inorganic selenite, wherein the salt of the inorganic selenite is sodium selenite, wherein the salt of inorganic selenite is administered orally; and
 administering radiotherapy to the subject within 6 hours after administering the salt of an inorganic selenite;
 wherein administering the salt of inorganic selenite and the radiotherapy provides for a synergistic effect in prostate cancer cell growth inhibition to treat the prostate cancer.

18. The method of claim 17, wherein the radiotherapy comprises external radiation therapy, brachytherapy (internal radiation therapy), or systemically targeted radiation.

19. The method of claim 17, wherein the salt of the inorganic selenite is administered within 2 hours prior to administering the radiotherapy.

20. The method of claim 17, wherein the prostate cancer is androgen-responsive.

21. The method of claim 17, wherein the prostate cancer is androgen-resistant.

* * * * *